(12) United States Patent
Robinson et al.

(10) Patent No.: US 8,969,415 B2
(45) Date of Patent: Mar. 3, 2015

(54) INTRAOCULAR DRUG DELIVERY SYSTEMS

(75) Inventors: Michael R. Robinson, Irvine, CA (US); Wendy M. Blanda, Tustin, CA (US); Patrick M. Hughes, Aliso Viejo, CA (US); Guadalupe Ruiz, Corona, CA (US); Werhner C. Orilla, Anaheim, CA (US); Scott M. Whitcup, Laguna Hills, CA (US); Devin F. Welty, Foothill Ranch, CA (US); Joan-En Lin, Tustin, CA (US); Lon T. Spada, Walnut, CA (US)

(73) Assignee: Allergan, Inc., Irvine, CA (US)

( * ) Notice: Subject to any disclaimer, the term of this patent is extended or adjusted under 35 U.S.C. 154(b) by 1925 days.

(21) Appl. No.: 11/565,917

(22) Filed: Dec. 1, 2006

(65) Prior Publication Data

US 2008/0131484 A1 Jun. 5, 2008

(51) Int. Cl.
| | |
|---|---|
| *A61K 31/165* | (2006.01) |
| *A61F 2/00* | (2006.01) |
| *A61K 31/565* | (2006.01) |
| *A61F 9/00* | (2006.01) |
| *A61K 9/00* | (2006.01) |
| *A61K 9/16* | (2006.01) |
| *A61K 9/50* | (2006.01) |
| *A61K 31/498* | (2006.01) |
| *A61K 31/557* | (2006.01) |
| *A61K 9/10* | (2006.01) |

(52) U.S. Cl.
CPC ............. *A61K 31/565* (2013.01); *A61F 9/0017* (2013.01); *A61K 9/0051* (2013.01); *A61K 9/1635* (2013.01); *A61K 9/1694* (2013.01); *A61K 9/5031* (2013.01); *A61K 31/498* (2013.01); *A61K 31/557* (2013.01); *A61K 9/10* (2013.01); *Y10S 514/913* (2013.01)
USPC ............................ 514/622; 514/913; 424/428

(58) Field of Classification Search
USPC .................................. 514/622, 913; 424/428
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 3,986,510 A | 10/1976 | Higuchi | |
| 4,008,864 A | 2/1977 | Torphammar et al. | |
| 4,014,335 A | 3/1977 | Arnold | |
| 4,052,505 A | 10/1977 | Higuchi et al. | |
| 4,057,619 A | 11/1977 | Higuchi et al. | |
| 4,063,064 A | 12/1977 | Saunders et al. | |
| 4,088,864 A | 5/1978 | Theeuwes et al. | |
| 4,144,317 A | 3/1979 | Higuchi et al. | |
| 4,158,005 A | 6/1979 | Bodor et al. | |
| 4,186,184 A | 1/1980 | Zaffaroni | |
| 4,190,642 A | 2/1980 | Gale et al. | |
| 4,200,098 A | 4/1980 | Ayer et al. | |
| 4,281,654 A | 8/1981 | Shell et al. | |
| 4,285,987 A | 8/1981 | Ayer et al. | |
| 4,303,637 A | 12/1981 | Shell et al. | |
| 4,304,765 A | 12/1981 | Shell et al. | |
| 4,327,725 A | 5/1982 | Cortese et al. | |
| 4,396,625 A | 8/1983 | Yamamori et al. | |
| 4,425,346 A | 1/1984 | Horlington et al. | |
| 4,474,451 A | 10/1984 | Mizokami et al. | |
| 4,478,818 A | 10/1984 | Shell et al. | |
| 4,494,274 A | 1/1985 | Thurlow | |
| 4,521,210 A | 6/1985 | Wong | |
| 4,599,353 A | 7/1986 | Bito | |
| 4,649,151 A | 3/1987 | Dougherty et al. | |
| 4,656,186 A | 4/1987 | Bommer et al. | |
| 4,668,506 A | 5/1987 | Bawa | |
| 4,675,338 A | 6/1987 | Bommer et al. | |
| 4,693,885 A | 9/1987 | Bommer et al. | |
| 4,712,500 A | 12/1987 | Montandon et al. | |
| 4,853,224 A | 8/1989 | Wong | |
| 4,863,457 A | 9/1989 | Lee | |
| 4,865,846 A | 9/1989 | Kaufman | |
| 4,866,168 A | 9/1989 | Dougherty et al. | |
| 4,932,934 A | 6/1990 | Dougherty et al. | |
| 4,935,498 A | 6/1990 | Sessler et al. | |
| 4,959,217 A | 9/1990 | Sanders et al. | |
| 4,968,715 A | 11/1990 | Dougherty et al. | |
| 4,981,871 A | 1/1991 | Abelson | |
| 4,997,652 A | 3/1991 | Wong | |
| 5,002,962 A | 3/1991 | Pandey et al. | |
| 5,017,579 A | 5/1991 | Gubin et al. | |
| 5,019,400 A | 5/1991 | Gombotz et al. | |
| 5,028,621 A | 7/1991 | Dougherty et al. | |
| 5,034,413 A | 7/1991 | Chan et al. | |
| 5,075,115 A | 12/1991 | Brine | |
| 5,089,509 A | 2/1992 | Chandraratna | |
| 5,093,349 A | 3/1992 | Pandey et al. | |
| 5,100,431 A | 3/1992 | Buster et al. | |
| 5,164,188 A | 11/1992 | Wong | |
| 5,169,638 A | 12/1992 | Dennis et al. | |

(Continued)

FOREIGN PATENT DOCUMENTS

| | | |
|---|---|---|
| CA | 1333770 | 1/1995 |
| EP | 0430539 | 6/1991 |

(Continued)

OTHER PUBLICATIONS

MerckSource, Dorland's Medical Dictionary-Analgoue, 2007, printed Feb. 17, 2009 from http://www.mercksource.com/pp/us/cns/cns_hl_dorlands_split.jsp?pg=/ppdocs/us/common/dorlands/dorland/one/000004228.htm, 2 pages.*

(Continued)

*Primary Examiner* — Gigi Huang
(74) *Attorney, Agent, or Firm* — Barbara C. Potts

(57) ABSTRACT

Biodegradable implants sized and suitable for implantation in an ocular region or site and methods for treating ocular conditions. The implants provide an extended release of an active agent at a therapeutically effective amount for a period of time between 10 days and one year or longer.

2 Claims, 5 Drawing Sheets

(56) References Cited

U.S. PATENT DOCUMENTS

| | | |
|---|---|---|
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,264,188 A | 11/1993 | Lew |
| 5,268,178 A | 12/1993 | Calhoun et al. |
| 5,300,114 A | 4/1994 | Gwon et al. |
| 5,314,905 A | 5/1994 | Pandey et al. |
| 5,356,629 A | 10/1994 | Sander et al. |
| 5,378,475 A | 1/1995 | Smith et al. |
| 5,385,887 A | 1/1995 | Yim et al. |
| 5,438,071 A | 8/1995 | Clauss et al. |
| 5,443,505 A | 8/1995 | Wong |
| 5,459,159 A | 10/1995 | Pandey et al. |
| 5,466,233 A | 11/1995 | Weiner et al. |
| 5,501,856 A | 3/1996 | Ohtori |
| 5,504,074 A | 4/1996 | D'Amato et al. |
| 5,516,522 A | 5/1996 | Peyman et al. |
| 5,587,371 A | 12/1996 | Sessler et al. |
| 5,587,479 A | 12/1996 | Makovec et al. |
| 5,597,897 A | 1/1997 | Ron et al. |
| 5,655,832 A | 8/1997 | Pelka et al. |
| 5,656,297 A | 8/1997 | Bernstein et al. |
| 5,688,819 A | 11/1997 | Woodward et al. |
| 5,707,643 A | 1/1998 | Ogura et al. |
| 5,716,918 A | 2/1998 | Sivik et al. |
| 5,766,242 A | 6/1998 | Wong |
| 5,770,589 A | 6/1998 | Billson et al. |
| 5,776,699 A | 7/1998 | Klein et al. |
| 5,798,349 A | 8/1998 | Levy et al. |
| 5,824,072 A | 10/1998 | Wong |
| 5,824,074 A | 10/1998 | Koch et al. |
| 5,856,329 A | 1/1999 | Wheeler |
| 5,869,079 A | 2/1999 | Wong |
| 5,877,207 A | 3/1999 | Klein et al. |
| 5,882,682 A | 3/1999 | Rork et al. |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 6,046,187 A | 4/2000 | Berde |
| 6,051,576 A | 4/2000 | Ashton et al. |
| 6,066,675 A | 5/2000 | Wen et al. |
| 6,074,661 A | 6/2000 | Olejnik et al. |
| 6,194,415 B1 | 2/2001 | Wheeler |
| 6,217,869 B1 | 4/2001 | Meyer et al. |
| 6,217,895 B1 | 4/2001 | Guo |
| 6,225,303 B1 | 5/2001 | Miller et al. |
| 6,248,741 B1 | 6/2001 | Wheeler |
| 6,256,319 B1 | 7/2001 | Hearst et al. |
| 6,270,492 B1 | 8/2001 | Sinofsky |
| 6,270,749 B1 | 8/2001 | Blumenkranz et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,306,426 B1 | 10/2001 | Olejnik et al. |
| 6,309,669 B1 | 10/2001 | Setterstrom et al. |
| 6,317,616 B1 | 11/2001 | Glossop |
| 6,319,273 B1 | 11/2001 | Chen et al. |
| 6,331,313 B1 | 12/2001 | Wong et al. |
| 6,357,568 B1 | 3/2002 | Chen et al. |
| 6,369,116 B1 | 4/2002 | Wong |
| 6,403,649 B1 | 6/2002 | Woodward et al. |
| 6,413,245 B1 | 7/2002 | Yaacobi et al. |
| 6,455,062 B1 | 9/2002 | Olejnik et al. |
| 6,465,464 B2 | 10/2002 | Wheeler |
| 6,482,854 B1 | 11/2002 | Lipton et al. |
| 6,497,729 B1 | 12/2002 | Moussy et al. |
| 6,537,568 B2 | 3/2003 | Olejnik et al. |
| 6,548,078 B2 | 4/2003 | Guo et al. |
| 6,565,871 B2 | 5/2003 | Roser et al. |
| 6,573,280 B2 | 6/2003 | Dreyer |
| 6,595,945 B2 | 7/2003 | Brown |
| 6,699,493 B2 | 3/2004 | Wong |
| 6,713,081 B2 | 3/2004 | Robinson et al. |
| 6,726,918 B1 | 4/2004 | Wong et al. |
| 6,765,012 B2 | 7/2004 | Andrews et al. |
| 6,899,717 B2 | 5/2005 | Weber |
| 7,090,681 B2 | 8/2006 | Weber |
| 7,771,742 B2 | 8/2010 | Hughes et al. |
| 7,799,336 B2 | 9/2010 | Hughes |
| 7,993,634 B2 | 8/2011 | Hughes et al. |
| 8,147,865 B2 | 4/2012 | Huang et al. |
| 8,206,736 B2 | 6/2012 | Hughes |
| 8,206,737 B2 | 6/2012 | Hughes |
| 8,445,027 B2 | 5/2013 | Hughes et al. |
| 2001/0023363 A1 | 9/2001 | Harth et al. |
| 2002/0032201 A1 | 3/2002 | Olejnik et al. |
| 2002/0035264 A1 | 3/2002 | Kararli et al. |
| 2002/0040015 A1 | 4/2002 | Miller et al. |
| 2002/0094998 A1 | 7/2002 | Burke et al. |
| 2002/0103255 A1 | 8/2002 | Hellberg et al. |
| 2003/0018078 A1 | 1/2003 | Woodward et al. |
| 2003/0069286 A1 | 4/2003 | Chen et al. |
| 2003/0095995 A1 | 5/2003 | Wong et al. |
| 2003/0175324 A1* | 9/2003 | Robinson et al. ............ 424/427 |
| 2003/0199478 A1 | 10/2003 | Andrews et al. |
| 2003/0203030 A1 | 10/2003 | Ashton et al. |
| 2003/0225152 A1 | 12/2003 | Andrews et al. |
| 2004/0054374 A1 | 3/2004 | Weber et al. |
| 2004/0058313 A1 | 3/2004 | Abreu |
| 2004/0137059 A1 | 7/2004 | Nivaggioli et al. |
| 2004/0151753 A1 | 8/2004 | Chen et al. |
| 2004/0175410 A1 | 9/2004 | Ashton et al. |
| 2004/0208910 A1 | 10/2004 | Ashton et al. |
| 2005/0107463 A1 | 5/2005 | Woodward et al. |
| 2005/0154399 A1 | 7/2005 | Weber |
| 2005/0203542 A1 | 9/2005 | Weber |
| 2005/0244458 A1 | 11/2005 | Huang et al. |
| 2005/0244461 A1 | 11/2005 | Nivaggioli et al. |
| 2005/0244462 A1 | 11/2005 | Fardoq |
| 2005/0244463 A1 | 11/2005 | Huang |
| 2005/0244464 A1* | 11/2005 | Hughes ........................ 424/427 |
| 2005/0244465 A1 | 11/2005 | Nivaggioli et al. |
| 2005/0244466 A1 | 11/2005 | Whitcup et al. |
| 2005/0244468 A1 | 11/2005 | Huang et al. |
| 2005/0244469 A1 | 11/2005 | Whitcup et al. |
| 2005/0244471 A1 | 11/2005 | Shiah |
| 2005/0244478 A1 | 11/2005 | Hughes et al. |
| 2005/0244479 A1 | 11/2005 | Hughes et al. |
| 2005/0244506 A1 | 11/2005 | Burke |
| 2005/0271705 A1 | 12/2005 | Hughes et al. |
| 2005/0281861 A1 | 12/2005 | Hughes et al. |
| 2006/0153786 A1 | 7/2006 | Kochinke et al. |
| 2006/0182781 A1 | 8/2006 | Hughes |
| 2006/0246145 A1 | 11/2006 | Chang et al. |
| 2006/0275230 A1 | 12/2006 | Kochinke et al. |
| 2007/0224246 A1 | 9/2007 | Hughes et al. |
| 2008/0033351 A1 | 2/2008 | Trogden et al. |
| 2008/0107694 A1 | 5/2008 | Trogden et al. |
| 2008/0145403 A1 | 6/2008 | Spada et al. |
| 2009/0081277 A1 | 3/2009 | Robinson et al. |
| 2010/0124565 A1 | 5/2010 | Spada et al. |
| 2010/0278898 A1 | 11/2010 | Hughes et al. |
| 2012/0122821 A1 | 5/2012 | Huang et al. |

FOREIGN PATENT DOCUMENTS

| | | |
|---|---|---|
| EP | 0 488 401 | 6/1992 |
| EP | 0490305 | 6/1992 |
| EP | 0 430 539 | 10/1994 |
| EP | 0 654 256 | 5/1995 |
| EP | 0364417 | 1/2002 |
| WO | WO 94/14117 | 7/1994 |
| WO | WO 95/13765 | 5/1995 |
| WO | WO 95/015748 | 6/1995 |
| WO | WO-96/38174 | 12/1996 |
| WO | WO 99/05263 | 2/1999 |
| WO | WO-00/04899 | 2/2000 |
| WO | WO-01/30323 | 5/2001 |
| WO | WO-01/58240 | 8/2001 |
| WO | WO-02/02076 | 1/2002 |

(56) References Cited

FOREIGN PATENT DOCUMENTS

| WO | WO 02/005815 | 1/2002 |
|---|---|---|
| WO | WO 02/09787 | 2/2002 |
| WO | WO-02/43785 | 6/2002 |
| WO | WO 02/085248 | 10/2002 |
| WO | WO-03/013477 | 2/2003 |
| WO | WO 03/024420 | 3/2003 |
| WO | WO-03/047513 | 6/2003 |
| WO | WO-03/074038 | 9/2003 |
| WO | WO-03/103772 | 12/2003 |
| WO | WO-2004/014352 | 2/2004 |
| WO | WO 2004/019938 | 3/2004 |
| WO | 2005/110362 | 11/2005 |
| WO | 2005/110364 | 11/2005 |
| WO | 2005/110368 | 11/2005 |
| WO | 2006/122165 | 11/2006 |
| WO | 2008/070402 | 6/2008 |

OTHER PUBLICATIONS

U.S. Appl. No. 10/666,872, filed Sep. 18, 2003, Weber.
U.S. Appl. No. 11/395,019, filed Mar. 31, 2006, Chang.
U.S. Appl. No. 11/303,462, filed Dec. 15, 2005, Hughes.
U.S. Appl. No. 11/371,118, filed Mar. 8, 2006, Chang.
Asbell P.A., et al., *Effects of topical antiglaucoma medications on the ocular surface*, Ocul Surf Jan. 2005;3(1):27-40.
Bloch-Michel E. (1992). *Opening address: intermediate uveitis*, In Intermediate Uveitis, Dev. Ophthalmol, W.R.F. Böke et al. editors, Basel: Karger, 23:1-2.
Bodor, N. et al. (1992), *A comparison of intraocular pressure elevating activity of loteprednol etabonate and dexamethasone in rabbits*, Current Eye Research 11:525-30.
Böke, W. (1992). *Clinical picture of intermediate uveitis*, In Intermediate Uveitis, Dev. Ophthalmol. W.R.F. Böke et al. editors, Basel: Karger, 23:20-7.
Cheng C-K et al. (1995), *Intravitreal sustained-release dexamethasone device in the treatment of experimental uveitis*, Inbest. Ophthalmol. Vis. Sci. 36:442-53.
Heller, *Biodegradable Polymers in Controlled Drug Delivery*, In: "CRC Critical Reviews in Therapeutic Drug Carrier Systems", vol. 1. CRC Press, Boca Raton, FL (1987).
Kwak, H.W. and D'Amico, D. J. (1992), *Evaluation of the retinal toxicity and pharmacokinetics of dexamethasone after intravitreal injection*, Arch. Ophthalmol. 110:259-66.
Lee, V.H.L. et al. (1989), *Drug delivery to the posterior segment* Chapter 25 In Retina. T.E. Ogden and A.P. Schachat eds., St. Louis: CV Mosby, vol. 1, pp. 483-498.
Maurice, D.M. (1983) *Micropharmaceutics of the eye*, Ocular Inflammation Ther. 1:97-102.
Mueller M., et al., *Tear film break up time and Schirmer test after different antiglaucomatous medications*, Invest Ophthalmol Vis Sci Mar. 15, 2000;41(4):S283.
Olsen, T.W. et al. (1995), *Human scleral permeability: effects of age, cryotherapy, transscleral diode laser, and surgical thinning*, Invest. Ophthalmol. Vis. Sci. 36:1893-1903.
Pinar, V., et al. (2005). *Intermediate Uveitis*, Immunology and Uveitis Service, Mass. Eye & Ear Infirmary, pp. 1-8.
Rao, N.A. et al. (1997), *Intraocular inflammation and uveitis, In Basic and Clinical Science Course*, Section 9 (1997-1998) San Francisco: American Academy of Ophthalmology, pp. 57-80, 102-103, 152-156.
Renfro, L. et al. (1992), *Ocular effects of topical and systemic steroids*, Dermatologic Clinics 10:505-12.
Schwartz, B., (1966) *The response of ocular pressure to corticosteroids*, Ophthalmol. Clin. North Am. 6:929-89.
Skalka, H.W. et al., (1980), *Effect of corticosteroids on cataract formation*, Arch Ophthalmol 98:1773-7.
Tracy et al., *Biomaterials* 20:1057-1062 (1999).
USP 23; NF 18 (1995) pp. 1790-1798.
Zhou, T, et al. (1998), *Development of a multiple-drug delivery implant for intraocular management of proliferative vitreoretinopathy*, Journal of Controlled Release 55: 281-295.
Enyedl, Laura et al., An Intravitreal Device Providing Sustained Released of Cyclosporine and Dexamethasone, Current Eye Research (1995) pp. 549-557.
Hainsworth, Dean P. et al., *Sustained Release Intravitreal Dexamethasone*, Journal of Ocular Pharmacology and Therapeutics, (1996) vol. 12, No. 1, pp. 57-63.
Anderson et al., "An Injectable Sustained Release Fertility Control System", Contraception, vol. 13, pp. 375-384 (1976).
Baker, R., "Controlled Release of Biologically Active Agents," A Wiley-Interscience Publication, p. 73-75 (1987).
Bito, L.Z., *Applied Pharmacology in the Medical Treatment*, Dance, S.M. and Neufeld, A.H. eds., New York, Grune & Stratton, 1984, pp. 477-505.
Bito, L.Z., "Prostaglandins, Old Concepts and New Perspectives" Arch. Ophthalmol. vol. 105, pp. 1036-1039 (1987).
Brubaker, "Mechanism of Action of Bimatoprost (Lumigan™)," *Surv Ophthalmol* 45 (Suppl 4): S347-S351 (2001).
Busse et al., "Tyrosine Kinase Inhibitors: Rationale, Mechanisms of Action, and Implications for Drug Resistance," Semin Oncol 28 (suppl 16) 47-55 (2001).
Phillips et al., "Penetration of Timolol Eye Drops into Human Aqueous Humour: The First Hour," *British Journal of Ophthalmology*, vol. 69, pp. 217-218 (1985).
Chen et al., "Lumigan®: A Novel Drug of Glaucoma Therapy," *Optom in Pract*, 3:95-102 (2002).
Chiang et al., "Pharmacokinetics and intraocular Pressure Lowering Effect of Timolol Preparations in Rabbit Eyes," *Journal of Ocular Pharmacology and Therapeutics*, vol. 12, No. 4, pp. 471-480, (1996).
Coleman et al., "A 3-Month Randomized Controlled Trial of Bimatoprost (LUMIGAN) Versus Combined Timolol and Dorzolamide (Cosopt) in Patients with Glaucoma or Ocular Hypertension," *Ophthalmology* 110(12):2362-8 (2003).
Coquelet et al., "Successful Photodynamic Therapy Combimed with Laser Photocoagulation in Three Eyes with Classic Subfoveal Choroidal Neovascularization Affecting Two Patients with Multifocal Choroiditis: Case Reports," Bull. Soc. Belge Ophtalmol, 283, 69-73, 2002.
Di Colo, "Controlled Drug Release From Implantable Matrices Based on Hydrophobic Polymers," *Biomaterials*, vol. 13, No. 12, pp. 850-856 (1992).
David L. Epstein, "Primary Open-Angle Glaucoma," *Chandler and Grant's Glaucoma*, Lea & Febiger, 1986, pp. 129-181.
Fabbro et al., "Protein Tyrosine Kinase Inhibitors: New Treatment Modalities?", *Current Opinion in Pharmacology*, 2:374-381 (2002).
Fotsis et al., "The Endogenous Oestrogen Metabolite 2-methoxyoestradiol Inhibits Angiogenesis and Suppresses Tumour Growth," *Nature* 1994, pp. 368, 237.
Goel et al., "Tyrosine Kinase Inhibiors: A Clinical Perspective," *Current Oncology Reports*, 4:9-19 (2002).
Guenther, Lyn C., "Optimizing Treatment with Topical Tazarotene," *Am. J. Clin. Dermotol.*, 2003:4(3):197-202.
Haluska et al., "Receptor Tyrosine Kinase Inhibitors," Current Opinion in Investigational Drugs, 2 (2):280-286 (2001).
Hare et al., "Efficacy and Safety of Memantine, an NMDA-Type Open-Channel Blocker, from Reduction of Retinal Injury associated with Experimental Glaucoma in Rat and Monkey," Surv Ophthalmol 45(Suppl 3): S284-S289 (2001), Plug of Biodegradable Polymers.
Hashizoe, Mototane et al., "Scleral for Controlled Drug Release in the Vitreous," *Arch Ophthalmol.* 1994; 112: 1380-1384.
Heller, *Hydrogeis in Medicine and Pharmacy*, N.A. Peppes ed., vol. III, (CRC Press, Boca Raton, FL, 1987), pp. 137-149.
Hoyng et al., "Pharmacological Therapy for Glaucoma," Drugs, Mar. 2000, 59(3):411-34.
Hubbard et al., "Protein Tyrosine Kinase Structure and Function," Annu. Rev. Biochem., 69: 373-98 (2000).
Jackanicz et al., "Polyactic Acid as a Biodegradable Carrier for Contraceptive Steriods" Contraception, vol. 8, No. 3:227-235 (1973).
Kimura, Hideya et al., "A New Vitreal Drug Delivery System Using an Implantable Biodegradable Polymeric Device," Invest Ophthalmol Vis Sci. 1994; 35: 2815-2819.

(56) References Cited

OTHER PUBLICATIONS

Kochinke et al., "Biodegradable Drug Delivery System for Uveitis Treatment," *Investigative Ophthalmology & Visual Science*, Feb. 15, vol. 37, No. 3, (1996).
Lai et al., "Alpha-2 Adrenoceptor Agonist Protects Retinal Function After Acute Retinal Ischemic Injury in the Rat," *Vis Neurosci*, 19:175-185 (2002).
Marks, R., "Topical Tazarotene: Review and Re-Evaluation," Retinoids, 2001; 17(3): 72-74.
Miller et al., "Degradation Rates of Oral Resorbabie Implants (Polylactates and Polyglycolates): Rate Modification with Changes in PLA/PGA Copolymer Ratios," *J. Biomed. Materials Res.* vol. 11, pp. 711-719 (1977).
Miller et al., "Synthesis and Structure-Activity Profiles of A-Hornoestranes, the Estratopones," J. Med. Chem., 40:3836-3841 (1997).
Olsen, T.W. et al., "Human Scleral Permeability: Effects of Age, Cryotherapy, Transscleral Diode Laser, and Surgical Thinning," *Invest. Ophthamol. Vis. Sci.* 36:1893-1903, 1995.
Phillips et al., "Efficacy of 0.1% Tazarotene Cream of the Treatment of Photodamage," *Arch Dermatol*, Nov. 2002, 138 (11): 1486-1493.
Pribtuda et al. "2-Methoxyestradiol: An Endogenous Antiangionic Antiproliferative Drug Candidate," Cancer and Metastasis Reviews, 19:173-179 (2000).
Quigley et al., "The Mechanism of Optic Nerve Damage in Experimental Acute Intraocular Pressure Elevation," Invest. Ophthalmol. Vis. Sci. 19:(1980), 505-517.
Schuettaui et al., "Effects of anti-glaucoma Medications on Ganglion Cell Survival: the DBA/2J Mouse Model," *Vision Res.*, 42(20):2333-7 (2002).
Schumacher et al., "The Physiological Estrogen Metabolite 2-Methoxyestradiol Reduced Tumor Growth and Induces Apoptosis in Human Solid Tumors," *J Cancer Res Clin Oncol.*, 127:405-410 (2001).
Stan, M.S., "Further Studies on the Effect of Prostaglandis on Intraocular Pressure in the Rabbit," *Exp. Eye Res.*, vol. 11, pp. 170-177 (1971).
Siebold et al., (1989), Ocul Surg News, 7(3), pp. 3 and 59.
Watson et al., "A Six-month, Randomized, Doulbe-masked Study Comparing Latanoprost with Timolol in Open-angle Glaucoma and Ocular Hypertension," *Ophthamology*, vol. 103:126-137 (1996).
Wheeler, "Experimental Studies of Agents with Potential Neuroprotective Properties," Acta Ophthalmol Scand, 77(229): 27-28 (1999).
Wheeler et al., "Role of Alpha-2 Agonists in Neuropretection," Surv Ophthalmol, vol. 48 (Suppl 1): S47-S51 (Apr. 2003).
WoldeMussie, "Neuroprotection of Retinal Ganglion Cells in Experimental Models of Glaucoma," Minerva Oftalmol, 42 (2): 71-8 (2000).
WoldeMussie, "Neuroprotection Effects of Memantine in Different RetinalINjury Models in Rats," J Glaucoma, 11 (6): 474-480 (2002).
Woodward et al., AGN 192024 (Lumigan®): A Synthetic Prostamide Analog that Lowers Primate Intraocular Pressure by Virtue of its Inherent Pharmacological Activity, ARVO 2002: (CD-ROM):POS, abstract only, 1 page.
Woodward et al., The Pharmacolgy of Bimatoprost (Lumigan™), Surv Ophthalmol (Suppl 4) S337-S345 (2001).
Bito, L.Z. Biological Protection with Prostaglandins Cohen, M.M., ed., Boca Raton, Fla., CRC Press Inc., 1985, pp. 231-252.
Charles et al., "Use of Bioerodible Polymers Impregnated with Mitomycin in Glaucoma Filtration Surgery in Rabbits," *Ophthalmology*, Apr. 1991, vol. 98, No. 4:503-508.
Jampel et al., "Glaucoma Filtration Surgery in Monkeys Using 5-Fluorouridine in Polyanhydride Disks," *Arch Ophthalmol.*, Mar. 1990, vol. 108:430-435.
Lee et al., "Glaucoma Filtration Surgey in Rabbits Using Bioerodible Polymers and 5-Fluorouacil," Ophthalmology, Dec. 1987, vol. 94, No. 12, pp. 1523-1530.
Lee et al., "The Use of Bioerodible Polymers and 5-Fluorouracils in Glaucoma Filtration Surgery," *Investigative Ophthalmology & Visual Science*, Nov. 1988, vol. 29, No. 11:1692-1697.
Smith et al., "Sustained-Release Subconjunctival 5-Fluorouracil," *Ophthalmic Surgery and Laser*, Sep. 1996, vol. 27, No. 9, pp. 763-767.
ALPHAGAN® P, Product Information, 2005.
*Company News on Call*, "Oculex Announces Positive Clinical Results for Posurdex(R)—The First Biodegradable Ocular Implants in Clinical Trail," Copyright © 1996-2004 PR Newswire Association LLC., 3 pages.
Lumigan®: A New Ocular Hypotensive Agent for Achieving Target Intraocular Pressures, Acta Ophthalmol Scand, Scientific Abstracts 2002: 80(4):457 (2002).
"Lumigan Found Effective in Early Phase 3," Ocul. Surg. News Mar. 1, 2001; 19 (5): 1, 35.
*Physician's Desk Reference*, product Information on "Alphagan®P," 54 Edition, (2001) pp. 493-494.
Physician's Desk Reference for Ophthalmic Medicines, 30 Edition, (2002) p. 285.
Surv Ophthalmol 2002; 47(3): p. 295.
TAZORAC®, Allergan, Product Information, 2004.
"Tazarolene," Drugs Future, 2003; 28 (2):208-209. Annual Update 2003: Dematologic Drugs.
Moshfeghi et al, "Retinal and Choroidal Vascular Occlusion After Posterior Sub-Tenon Triamcinolone Injection", American Journal of Ophthalmology, vol. 134, Issue 1, 2002, pp. 132-134.
Stewart et al, "The Efficacy and Safety of Latanoprost 0.005% Once Daily Versus Brimonidine 0.2% Twice Daily in Open-Angle Glaucoma or Ocular Hypertension", American Journal of Ophthalmology, vol. 131, Issue 5, 2001, pp. 631-635.
United States Board of Patent Appeals and Interferences decision on appeal in *Ex parte* Huang et al., Appeal No. 2010-006865, U.S. Appl. No. 10/836,880, mailed Sep. 28, 2010.
United States Board of Patent Appeals and Interferences decision on appeal in *Ex parte* Nivaggioli et al., Appeal No. 2009-013914, U.S. Appl. No. 10/340,237, mailed Sep. 21, 2010.
United States Board of Patent Appeals and Interferences decision on appeal in *Ex parte* Huang et al., Appeal No. 2010-004999, U.S. Appl. No. 10/836,911, mailed Oct. 25, 2010.
Wine et al. (1964) "The ocular uptake of subconjunctivally injected C14 hydrocortisone" Am. J. Ophthalmol. 58:362-6.
U.S. Appl. No. 11/859,310, filed Sep. 21, 2007.
Herrero-Vanrell et al. (2001) "Biodegradable microspheres for vitreoretinal drug delivery " *Adv. Drug Delivery Reviews* 52:5-16.
"Subconjunctival Injection", Chapter 97, pp. 432-435, in Atlas of Primary Eyecare Procedures, $2^{nd}$ Ed., Casser, Fingeret, and Woodcome, Copyright 1997 by Appleton & Lange.
Wine et al. (1964) "The ocular uptake of subconjunctivally injected $C^{14}$ hydrocortisone" *Am. J. Ophthalmol.* 58:362-6.

\* cited by examiner

INTRAOCULAR DRUG DELIVERY SYSTEMS

BACKGROUND

The present invention relates to drug delivery systems and methods for treating ocular conditions. In particular the present invention relates to systems and methods for treating an ocular condition by administering to an ocular region or site a sustained release drug delivery system which comprises a therapeutic agent and a bioerodible polymer.

An ocular condition can include a disease, aliment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. A front of the eye ocular condition is a disease, ailment or condition which affects or which involves an ocular region or site, such as a periocular muscle, an eye lid or an eye ball tissue or fluid which is located anterior to the posterior wall of the lens capsule or ciliary muscles. Thus, a front of the eye ocular condition primarily affects or involves, the conjunctiva, the cornea, the conjunctiva, the anterior chamber, the iris, the posterior chamber (behind the iris but in front of the posterior wall of the lens capsule), the lens and the lens capsule as well as blood vessels, lymphatics and nerves which vascularize, maintain or innervate an anterior ocular region or site.

A front of the eye ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can be considered to be a front of the eye ocular condition because a clinical goal of glaucoma treatment can be to reduce a hypertension of aqueous fluid in the anterior chamber of the eye (i.e. reduce intraocular pressure).

A posterior (back of the eye) ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, macular degeneration (such as non-exudative age related macular degeneration and exudative age related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can also be considered a posterior ocular condition because a therapeutic goal of glaucoma treatment is to prevent the loss of or reduce the occurrence of loss of vision due to damage to or loss of retinal cells or optic nerve cells (i.e. neuroprotection).

Macular degeneration, such as age related macular degeneration ("AMD") is a leading cause of blindness in the world. It is estimated that thirteen million Americans have evidence of macular degeneration. Macular degeneration results in a break down the macula, the light-sensitive part of the retina responsible for the sharp, direct vision needed to read or drive. Central vision is especially affected. Macular degeneration is diagnosed as either dry (atrophic) or wet (exudative). The dry form of macular degeneration is more common than the wet form of macular degeneration, with about 90% of AMD patients being diagnosed with dry AMD. The wet form of the disease usually leads to more serious vision loss. Macular degeneration can produce a slow or sudden painless loss of vision. The cause of macular degeneration is not clear. The dry form of AMD may result from the aging and thinning of macular tissues, depositing of pigment in the macula, or a combination of the two processes. With wet AMD, new blood vessels grow beneath the retina and leak blood and fluid. This leakage causes retinal cells to die and creates blind spots in central vision.

Macular edema ("ME") can result in a swelling of the macula. The edema is caused by fluid leaking from retinal blood vessels. Blood leaks out of the weak vessel walls into a very small area of the macula which is rich in cones, the nerve endings that detect color and from which daytime vision depends. Blurring then occurs in the middle or just to the side of the central visual field. Visual loss can progress over a period of months. Retinal blood vessel obstruction, eye inflammation, and age-related macular degeneration have all been associated with macular edema. The macula may also be affected by swelling following cataract extraction. Symptoms of ME include blurred central vision, distorted vision, vision tinted pink and light sensitivity. Causes of ME can include retinal vein occlusion, macular degeneration, diabetic macular leakage, eye inflammation, idiopathic central serous chorioretinopathy, anterior or posterior uveitis, pars planitis, retinitis pigmentosa, radiation retinopathy, posterior vitreous detachment, epiretinal membrane formation, idiopathic juxtafoveal retinal telangiectasia, Nd:YAG capsulotomy or iridotomy. Some patients with ME may have a history of use of topical epinephrine or prostaglandin analogs for glaucoma. The first line of treatment for ME is typically anti-inflammatory drops topically applied.

Diabetic retinopathy is the leading cause of blindness among adults aged 20 to 74 years. Macular ischemia is a major cause of irreversible vision acuity loss and decreased contrast sensitivity in patients with diabetic retinopathy. The capillary nonperfusion and decreased capillary blood flow that is responsible for this ischemia is seen clinically on the fluorescein angiogram as an increase in the foveal avascular zone (FAZ) or an irregularity of the outline of the FAZ. These findings are predictors of the other, perhaps more well-known, sight-threatening complications of diabetic retinopathy, including macular edema and proliferative retinopathy. Perhaps more importantly, extensive capillary nonperfusion is also a predictor of a poor visual prognosis from diabetic retinopathy.

There are treatments available or in development for macular edema and proliferative retinopathy, such as laser photocoagulation, intravitreal corticosteroids and anti-VEGF therapies. Although laser photocoagulation has been studied for vision loss directly associated with macular ischemia, there is currently no known treatment for this indication.

The exterior surface of the normal globe mammalian eye has a layer of tissue known as conjunctival epithelium, under which is a layer of tissue called Tenon's fascia (also called conjunctival stroma). The extent of the Tenon's fascia extending backwards across the globe forms a fascial sheath known as Tenon's capsule. Under Tenon's fascia is the episclera. Collectively, the conjunctival epithelium and the Tenon's fascia is referred to as the conjunctiva. As noted, under Tenon's fascia is the episclera, underneath which lies the sclera, followed by the choroid. Most of the lymphatic vessels and their associated drainage system, which is very efficient at removing therapeutic agents placed in their vicinity, is present in the conjunctiva of the eye.

A therapeutic agent can be administered to the eye to treat an ocular condition. For example the target tissue for an antihypertensive therapeutic agent to treat the elevated intraocular pressure characteristic of glaucoma can be the ciliary body and/or the trabecular meshwork. Unfortunately, administration of an ocular topical antihypertensive pharmaceutical in the form of eye drops can result in a rapid wash out of most if not all of the therapeutic agent before it reaches the ciliary body and/or the trabecular meshwork target tissue, thereby requiring frequent redosing to effectively treat a hypertensive condition. Additionally, side effects to patients from topical administration of antiglaucoma medications and their preservatives range from ocular discomfort to sight-threatening alterations of the ocular surface, including conjunctival hyperemia (eye redness), stinging, pain, decreased tear production and function, decreased tear film stability, superficial punctate keratitis, squamous cell metaplasia, and changes in cell morphology. These adverse effects of topical antiglaucoma eyedrops can interfere with the treatment of glaucoma by discouraging patient dosing compliance, and as well long-term treatment with eyedrops is associated with a higher failure of filtration surgery. Asbell P. A., et al., *Effects of topical antiglaucoma medications on the ocular surface*, Ocul Surf 2005 January; 3(1):27-40; Mueller M., et al., *Tear film break up time and Schirmer test after different antiglaucomatous medications*, Invest Ophthalmol Vis Sci 2000 Mar. 15; 41(4):S283.

It is known to administer a drug depot to the posterior (i.e. near the macula) sub-Tenon space. See eg column 4 of U.S. Pat. No. 6,413,245. Additionally, it is known to administer a polylactic implant to the sub-tenon space or to a suprachoroidal location. See eg published U.S. Pat. No. 5,264,188 and published U.S. patent application 20050244463.

An anti-inflammatory (i.e. immunosuppressive) agent can be used for the treatment of an ocular condition, such as a posterior ocular condition, which involves inflammation, such as an uveitis or macula edema. Thus, topical or oral glucocorticoids have been used to treat uveitis. A major problem with topical and oral drug administration is the inability of the drug to achieve an adequate (i.e. therapeutic) intraocular concentration. See e.g. Bloch-Michel E. (1992). *Opening address: intermediate uveitis*, In Intermediate Uveitis, Dev. Ophthalmol, W. R. F. Böke et al. editors, Basel: Karger, 23:1-2; Pinar, V., et al. (1997). *Intraocular inflammation and uveitis*" In Basic and Clinical Science Course. Section 9 (1997-1998) San Francisco: American Academy of Ophthalmology, pp. 57-80, 102-103, 152-156; Böke, W. (1992). *Clinical picture of intermediate uveitis*, In Intermediate Uveitis, Dev. Ophthalmol. W. R. F. Böke et al. editors, Basel: Karger, 23:20-7; and Cheng C-K et al. (1995), *Intravitreal sustained-release dexamethasone device in the treatment of experimental uveitis*, Invest. Ophthalmol. Vis. Sci. 36:442-53.

Systemic glucocorticoid administration can be used alone or in addition to topical glucocorticoids for the treatment of uveitis. However, prolonged exposure to high plasma concentrations (administration of 1 mg/kg/day for 2-3 weeks) of steroid is often necessary so that therapeutic levels can be achieved in the eye.

Unfortunately, these high drug plasma levels commonly lead to systemic side effects such as hypertension, hyperglycemia, increased susceptibility to infection, peptic ulcers, psychosis, and other complications. Cheng C-K et al. (1995), *Intravitreal sustained-release dexamethasone device in the treatment of experimental uveitis*, Invest. Ophthalmol. Vis. Sci. 36:442-53; Schwartz, B., (1966) *The response of ocular pressure to corticosteroids*, Ophthalmol. Clin. North Am. 6:929-89; Skalka, H. W. et al., (1980), *Effect of corticosteroids on cataract formation*, Arch Ophthalmol 98:1773-7; and Renfro, L. et al. (1992), *Ocular effects of topical and systemic steroids*, Dermatologic Clinics 10:505-12.

Additionally, delivery to the eye of a therapeutic amount of an active agent can be difficult, if not impossible, for drugs with short plasma half-lives since the exposure of the drug to intraocular tissues is limited. Therefore, a more efficient way of delivering a drug to treat a posterior ocular condition is to place the drug directly in the eye, such as directly into the vitreous. Maurice, D. M. (1983) *Micropharmaceutics of the eye*, Ocular Inflammation Ther. 1:97-102; Lee, V. H. L. et al. (1989), *Drug delivery to the posterior segment*" Chapter 25 In Retina. T. E. Ogden and A. P. Schachat eds., St. Louis: CV Mosby, Vol. 1, pp. 483-98; and Olsen, T. W. et al. (1995), *Human scleral permeability: effects of age, cryotherapy, transscleral diode laser, and surgical thinning*, Invest. Ophthalmol. Vis. Sci. 36:1893-1903.

Techniques such as intravitreal injection of a drug have shown promising results, but due to the short intraocular half-life of active agent, such as glucocorticoids (approximately 3 hours), intravitreal injections must be frequently repeated to maintain a therapeutic drug level. In turn, this repetitive process increases the potential for side effects such as retinal detachment, endophthalmitis, and cataracts. Maurice, D. M. (1983), *Micropharmaceutics of the eye, Ocular Inflammation Ther.* 1:97-102; Olsen, T. W. et al. (1995), *Human scleral permeability: effects of age, cryotherapy, transscleral diode laser, and surgical thinning*, Invest. Ophthalmol. Vis. Sci. 36:1893-1903; and Kwak, H. W. and D'Amico, D. J. (1992), *Evaluation of the retinal toxicity and pharmacokinetics of dexamethasone after intravitreal injection*, Arch. Ophthalmol. 110:259-66.

Additionally, topical, systemic, and periocular glucocorticoid treatment must be monitored closely due to toxicity and the long-term side effects associated with chronic systemic drug exposure sequelae. Rao, N. A. et al. (1997), *Intraocular inflammation and uveitis*, In *Basic and Clinical Science Course*, Section 9 (1997-1998) San Francisco: American Academy of Ophthalmology, pp. 57-80, 102-103, 152-156; Schwartz, B. (1966), *The response of ocular pressure to corticosteroids, Ophthalmol Clin North Am* 6:929-89; Skalka, H. W. and Pichal, J. T. (1980), *Effect of corticosteroids on cataract formation, Arch Ophthalmol* 98:1773-7; Renfro, L and Snow, J. S. (1992), *Ocular effects of topical and systemic steroids*, Dermatologic Clinics 10:505-12; Bodor, N. et al. (1992), *A comparison of intraocular pressure elevating activity of loteprednol etabonate and dexamethasone in rabbits, Current Eye Research* 11:525-30.

Known drug delivery systems which are placed in the vitreous or on the sclera are usually sutured in place at the sclera or have some attachment means to retain them in place so as to prevent them from becoming extruded or otherwise migrating from the original site due to the normal frequent movement of the eye. Extrusion can result in the drug delivery system eroding through the conjunctiva and being lost. Migration of the drug delivery system from its administration site can have the undesirable effect of either a suboptimal amount or an excessive amount of the therapeutic agent now reaching the target tissue.

An intraocular drug delivery system can be made of a biodegradable polymeric such as a poly(lactide) (PLA) polymers, poly(lactide-co-glycolide) (PLGA) polymers, as well as copolymers of PLA and PLGA polymers. PLA and PLGA polymers degrade by hydrolysis, and the degradation products, lactic acid and glycolic acid, are metabolized into carbon dioxide and water. General properties of the certain PLA and PLGA biodegradable polymers are shown in Table 1.

suggested that brimonidine can have a neuroprotective effect upon retinal cells. See eg U.S. Pat. Nos. 5,856,329; 6,194,415; 6,248,741, and; 6,465,464.

U.S. Pat. No. 6,217,895 discusses a method of administering a corticosteroid to the posterior segment of the eye, but does not disclose a bioerodible implant. U.S. Pat. No. 5,501,856 discloses controlled release pharmaceutical preparations for intraocular implants to be applied to the interior of the eye after a surgical operation for disorders in retina/vitreous body or for glaucoma. U.S. Pat. No. 5,869,079 discloses combinations of hydrophilic and hydrophobic entities in a biodegrad-

TABLE 1

General Properties of Certain Biodegradable Polymers

|  | PLA ester | PLA ester | 50:50 PLGA acid |
|---|---|---|---|
| Common Names | Resomer ® 203S, PLA, Poly (D,L-lactide), polylactic acid | Resomer ® 208, PLA, Poly (D,L-lactide), polylactic acid | Resomer ® RG 502H, PLG acid end, PLGA acid end, 50:50 Poly (D,L-lactide-co-glycolide) acid end |
| Structure | $\left[-O-\underset{H_3C}{\underset{|}{C}}\underset{H}{\overset{|}{C}}-O-\underset{\underset{O}{\|}}{C}-\underset{H_3C}{\underset{|}{C}}\underset{H}{\overset{|}{C}}-\underset{\underset{O}{\|}}{C}\right]_n -OR$ | $\left[-O-\underset{H_3C}{\underset{|}{C}}\underset{H}{\overset{|}{C}}-O-\underset{\underset{O}{\|}}{C}-\underset{H_3C}{\underset{|}{C}}\underset{H}{\overset{|}{C}}-\underset{\underset{O}{\|}}{C}\right]_n -OR$ | $\left[-\left[O-\underset{H_3C}{\underset{|}{C}}\underset{H}{\overset{|}{C}}-\underset{\underset{O}{\|}}{C}-O-\underset{H_3C}{\underset{|}{C}}\underset{H}{\overset{|}{C}}-\underset{\underset{O}{\|}}{C}\right]_x \left[O-\underset{H}{\underset{|}{C}}\underset{H}{\overset{|}{C}}-\underset{\underset{O}{\|}}{C}-O-\underset{H}{\underset{|}{C}}\underset{H}{\overset{|}{C}}-\underset{\underset{O}{\|}}{C}\right]_y\right]_n -OH$ |
|  | n = average number of repeating units<br>R = proprietary alkyl group | n = average number of repeating units<br>R = proprietary alkyl group | Where:<br>x = y = 1<br>n = average number of repeating units |
| CAS Number | 26680-10-4 | 26680-10-4 | 26780-50-7 |
| Empirical Formula | [(C6H8O4)n] | [(C6H8O4)n] | [(C6H8O4)x•(C4H4O4)y]OH<br>x:y = 50:50 |
| Inherent Viscosity, dl/g | 0.25-0.35 | 1.8-2.2 | 0.16-0.24 |
| Description | white to off white powder | white to off white powder | white to near white powder |

Drug delivery systems have been formulated with various active agents. For example, it is known to make 2-methoxyestradiol poly lactic acid polymer implants (as rods and wafers), intended for intraocular use, by a melt extrusion method. See eg published U.S. patent application 20050244471. Additionally, it is known to make brimonidine poly lactic acid polymer implants and microspheres intended for intraocular use. See eg published U.S. patent applications 20050244463 and 20050244506, and U.S. patent application Ser. No. 11/395,019. Furthermore, it is known to make bimatoprost containing polylactic acid polymer implants and microspheres intended for intraocular use. See eg published U.S. patent applications 2005 0244464 and 2006 0182781, and U.S. patent application Ser. Nos. 11/303,462, and; 11/371,118.

Brimonidine is an $\alpha_{2B}$-selective adrenergic agonist used to treat open-angle glaucoma by decreasing aqueous humor production and increasing uveoscleral outflow. The chemical structure of brimonidine tartrate is:

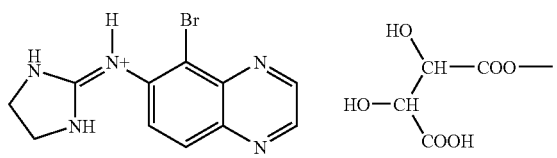

The chemical formula for brimonidine tartrate is F, 5-bromo-6-(2-imidazolidinylideneamino)quinoxaline tartrate $C_{15}H_{16}N_5O_6Br$ or $(C_{11}H_{10}BrN_5 \cdot C_4H_6O_6)$ Brimonidine tartrate has been used in ophthalmic solutions in concentrations of 0.2%, 0.15% and 0.1%. It has been able sustained release implant, and describes a polylactic acid polyglycolic acid (PLGA) copolymer implant comprising dexamethasone. As shown by in vitro testing of the drug release kinetics, the 100-120 µg 50/50 PLGA/dexamethasone implant disclosed did not show appreciable drug release until the beginning of the fourth week, unless a release enhancer, such as HPMC was added to the formulation.

U.S. Pat. No. 5,824,072 discloses implants for introduction into a suprachoroidal space or an avascular region of the eye, and describes a methylcellulose (i.e. non-biodegradable) implant comprising dexamethasone. WO 9513765 discloses implants comprising active agents for introduction into a suprachoroidal or an avascular region of an eye for therapeutic purposes. U.S. Pat. Nos. 4,997,652 and 5,164,188 disclose biodegradable ocular implants comprising microencapsulated drugs, and describes implanting microcapsules comprising hydrocortisone succinate into the posterior segment of the eye.

U.S. Pat. No. 5,164,188 discloses encapsulated agents for introduction into the suprachoroid of the eye, and describes placing microcapsules and plaques comprising hydrocortisone into the pars plana. U.S. Pat. Nos. 5,443,505 and 5,766,242 discloses implants comprising active agents for introduction into a suprachoroidal space or an avascular region of the eye, and describes placing microcapsules and plaques comprising hydrocortisone into the pars plana.

Zhou et al. disclose a multiple-drug implant comprising 5-fluorouridine, triamcinolone, and human recombinant tissue plasminogen activator for intraocular management of proliferative vitreoretinopathy (PVR). Zhou, T, et al. (1998), *Development of a multiple-drug delivery implant for*

*intraocular management of proliferative vitreoretinopathy*, Journal of Controlled Release 55: 281-295.

U.S. Pat. No. 6,046,187 discusses methods and compositions for modulating local anesthetic by administering one or more glucocorticosteroid agents before, simultaneously with or after the administration of a local anesthetic at a site in a patient. U.S. Pat. No. 3,986,510 discusses ocular inserts having one or more inner reservoirs of a drug formulation confined within a bioerodible drug release rate controlling material of a shape adapted for insertion and retention in the sac of the eye, which is indicated as being bounded by the surfaces of the bulbar conjuctiva of the sclera of the eyeball and the palpebral conjunctiva of the eyelid, or for placement over the corneal section of the eye.

U.S. Pat. No. 6,369,116 discusses an implant with a release modifier inserted in a scleral flap. EP 0 654256 discusses use of a scleral plug after surgery on a vitreous body, for plugging an incision. U.S. Pat. No. 4,863,457 discusses the use of a bioerodible implant to prevent failure of glaucoma filtration surgery by positioning the implant either in the subconjunctival region between the conjunctival membrane overlying it and the sclera beneath it or within the sclera itself within a partial thickness sclera flap.

EP 488 401 discusses intraocular implants, made of certain polylactic acids, to be applied to the interior of the eye after a surgical operation for disorders of the retina/vitreous body or for glaucoma. EP 430539 discusses use of a bioerodible implant which is inserted in the suprachoroid.

Intraocular drug delivery systems which are sutured or fixed in place are known. Suturing or other fixation means requires sensitive ocular tissues to be in contact with aspects of a drug delivery system which are not required in order to contain a therapeutic agent within or on the drug delivery system or to permit the therapeutic agent to be released in vivo. As such suturing or eye fixation means a merely peripheral or ancillary value and their use can increase healing time, patient discomfort and the risk of infection or other complications.

Thus, there is a need for a sustained release intraocular drug delivery system for the treatment of an ocular condition wherein the intraocular drug delivery system is not sutured or otherwise fixed in place and provides an effective dose of a therapeutic agent to the desired intraocular target tissue with little or no ocular surface hyperemia or other untoward side effects.

SUMMARY

The present invention meets these and other needs and provides a drug delivery system for the treatment of an ocular condition which can provide sustained release of a therapeutically effective amount of a therapeutic agent, wherein intraocular administration of the drug delivery system results in little or no ocular surface hyperemia.

DEFINITIONS

The terms below are defined to have the following meanings:

"About" means approximately or nearly and in the context of a numerical value or range set forth herein means±10% of the numerical value or range recited or claimed.

"Active agent", "drug" and "therapeutic agent" are used interchangeably herein and refer to any substance used to treat an ocular condition.

"Anterior intraocular location" with regard to a site of administration of a drug delivery system for treatment of an ocular hypertensive condition means a sub-Tenon, suprachoroidal, intrascleral, episcleral, and the like intraocular location which is located no more than about 10 mm (preferably no more than about 8 mm) along the curvature of the surface of the eye from the corneal limbus.

"Biocompatible" with regard to a drug delivery system means that upon intraocular administration of the drug delivery system to a mammalian eye, either no hyperemia is observed at and adjacent to the ocular surface into which the drug delivery system was administered or the hyperemia observed at and adjacent to the ocular surface into which the drug delivery system was administered is observed to be a normal or hi normal ocular surface hyperemia score within ten days after the intraocular administration of the drug delivery system and the ocular surface hyperemia remains an ocular surface hyperemia with a score of normal or hi normal for the remaining period for which the drug delivery system remains in situ at the intraocular location. The observed ocular surface hyperemia can determined using the Table 2 OSH scoring system.

"Bioerodible polymer" means a polymer which degrades in vivo. Drug delivery systems containing bioerodible polymers can have a triphasic pattern of drug release: an initial burst from surface bound drug; the second phase from diffusional release, and; release due to degradation of the polymer matrix. Thus, erosion of the polymer over time is required to release all of the active agent. Hence, hydrogels such as methylcellulose which act to release drug through polymer swelling are specifically excluded from the term "bioerodible (or biodegradable) polymer". The words "bioerodible" and "biodegradable" are synonymous and are used interchangeably herein.

"Cumulative release profile" means to the cumulative total percent of an active agent released from an implant into an ocular region or site in vivo over time or into a specific release medium in vitro over time.

"Drug delivery system" means a physical device from which a therapeutic amount of a therapeutic agent can be released upon in vivo administration of the drug delivery system. The drug delivery system can be an implant (which can be configured for example as a rod, cylinder, filament, fiber, disc or wafer) or a population of microspheres "Glaucoma" means primary, secondary and/or congenital glaucoma. Primary glaucoma can include open angle and closed angle glaucoma. Secondary glaucoma can occur as a complication of a variety of other conditions, such as injury, inflammation, vascular disease and diabetes.

"Inflammation-mediated" in relation to an ocular condition means any condition of the eye which can benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion.

"Injury" or "damage" are interchangeable and refer to the cellular and morphological manifestations and symptoms resulting from an inflammatory-mediated condition, such as, for example, inflammation.

"Intraocular" means within or under an ocular tissue. An Intraocular administration of a drug delivery system includes administration of the drug delivery system to a sub-Tenon, subconjunctival, suprachoroidal, intravitreal and like location. An Intraocular administration of a drug delivery system excludes administration of the drug delivery system to a topical, systemic, intramuscular, subcutaneous, intraperitoneal, and the like location.

"Measured under infinite sink conditions in vitro," means assays to measure drug release in vitro, wherein the experiment is designed such that the drug concentration in the receptor medium never exceeds 5% of saturation. Examples of suitable assays may be found, for example, in USP 23; NF 18 (1995) pp. 1790-1798.

"Ocular condition" means a disease, aliment or condition which affects or involves the eye or one or the parts or regions of the eye, such as a retinal disease. The eye includes the eyeball and the tissues and fluids which constitute the eyeball, the periocular muscles (such as the oblique and rectus muscles) and the portion of the optic nerve which is within or adjacent to the eyeball.

"Plurality" means two or more.

"Posterior ocular condition" means a disease, ailment or condition which affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Steroidal anti-inflammatory agent" and "glucocorticoid" are used interchangeably herein, and are meant to include steroidal agents, compounds or drugs which reduce inflammation when administered at a therapeutically effective level.

"Substantially" in relation to the release profile or the release characteristic of an active agent from a bioerodible implant as in the phrase "substantially continuous rate" of the active agent release rate from the implant means, that the rate of release (i.e. amount of active agent released/unit of time) does not vary by more than 100%, and preferably does not vary by more than 50%, over the period of time selected (i.e. a number of days). "Substantially" in relation to the blending, mixing or dispersing of an active agent in a polymer, as in the phrase "substantially homogenously dispersed" means that there are no or essentially no particles (i.e. aggregations) of active agent in such a homogenous dispersal.

"Suitable for insertion (or implantation) in (or into) an ocular region or site" with regard to an implant, means an implant which has a size (dimensions) such that it can be inserted or implanted without causing excessive tissue damage and without unduly physically interfering with the existing vision of the patient into which the implant is implanted or inserted.

"Sustained" as in "sustained period" or "sustained release" means for a period of time greater than thirty days, preferably for at least 20 days (i.e. for a period of time from 20 days to 365 days), and most preferably for at least 30 days. A sustained release can persist for a year or more.

"Therapeutic levels" or "therapeutic amount" means an amount or a concentration of an active agent that has been locally delivered to an ocular region that is appropriate to safely treat an ocular condition so as to reduce or prevent a symptom of an ocular condition.

Bioerodible implants according to the present invention can be are prepared using two or more different bioerodible polymers each having different release characteristics. In one variation, a first quantity of the drug or active agent is blended with a first polymer and the resultant material is extruded and then broken into particles which are then blended with an additional quantity of the drug or active agent and the same or a second polymer to form the final bioerodible implant, either by extrusion, injection molding or direct compression. The resultant implant has a release profile different than that of an implant created by initially blending the polymers together and provides for continual or substantially continual release of active agent at levels.

In yet further variations, active agent can be separately blended with first and second bioerodible polymers to form first and second drug-polymer mixtures that can be co-extruded to produce implants having first and second regions with differing release characteristics. The resultant implant has a release profile different than that of an implant created by initially blending the two polymers together and provides for continual release of drug. The implant can contain one or more active agents. Additionally, two active agents in the implant can be covalently attached to each other to form a pro-drug, which upon release from the implant dissociates into the two separate active agents. Furthermore, the implant can comprise rapid pore formers in the polymeric matrix of the implant, for example by the addition of methocel (a polymer with high solubility) to the polymeric matrix which is released soon after in vivo implantation. The pore former additive can act to create pores in the polymer matrix to thereby increase all phases of drug release and can be used to customize the release rate.

Our invention encompasses a drug delivery system for treating an ocular condition, the drug delivery system can comprise: (a) at least one bioerodible implant suitable for insertion into an ocular region or site, the bioerodible implant comprising; (i) an active agent, and; (ii) a bioerodible polymer, wherein the bioerodible implant can release a therapeutic level of the active agent into the ocular region or site for a period time between about 30 days and about 1 year. Preferably, the bioerodible implant can release the therapeutic level of the active agent into the ocular region or site at a substantially continuous rate in vivo. More preferably, the bioerodible implant can release a therapeutic level of the active agent into the ocular region or site at a substantially continuous rate upon implantation in the vitreous for a period time between about 50 days and about 1 year. The active agent can be an anti-inflammatory agent. The bioerodible polymer can be a PLGA co-polymer.

The bioerodible implant can have a weight between about 1 µg and about 100 mg and no dimension less than about 0.1 mm and no dimension greater than about 20 mm.

A drug delivery system of claim within the scope of our invention can comprise a plurality of bioerodible implants. The active agent can be substantially homogenously dispersed within the bioerodible polymer or the active agent can be associated with the bioerodible polymer in the form of particles of active agent and bioerodible polymer.

In a preferred embodiment the drug delivery system can comprise: (a) a portion of the active agent substantially homogenously dispersed within a portion of the bioerodible polymer, and; (b) a portion of the same or of a different active agent associated with a portion of same or of a different bioerodible polymer in the form of particles of active agent and the bioerodible polymer.

In a further embodiment the drug delivery system can comprise: (a) a bioerodible implant suitable for insertion into an ocular region or site, the bioerodible implant comprising; (i) an active agent, and; (ii) a bioerodible polymer, wherein the bioerodible implant can release a therapeutic level of the active agent upon insertion into a posterior ocular region or site for a period time of at least about 40 days.

Additionally, the drug delivery system can comprise: (a) a plurality of bioerodible implants implantable in a posterior ocular region or site, each implant comprising; (i) an active agent, and; (ii) a bioerodible polymer, wherein the plurality of bioerodible implants can substantially continuously release in vivo a therapeutic level of the active agent for a period time between about 5 days and about 1 year. This drug delivery system can comprise: (a) a first implant with a first release characteristic, and; (b) a second implant with a second release characteristic, wherein the first and second release characteristics differ. The release profile of the drug delivery system can correspond to the sum of the first and second release profiles. Notably, this drug delivery system can comprise: (a) a first implant with a first release characteristic, (b) a second implant with a second release characteristic, and; (c) a third implant with a third release characteristic. And the release profile of the drug delivery system can correspond to the sum of the first, second and third release profiles. The drug delivery system can comprise at least two different implants which have different bioerodible polymers. Thus, the drug deliver system can comprise first, second and third bioerodible implants, wherein the first implant comprises a first polymer with a first average molecular weight; the second implant comprises a second polymer with a second average molecular weight, and the third implant comprises a third polymer with a third average molecular weight.

A particular embodiment of our invention can be a drug delivery system for treating a ocular condition comprising; (a) a plurality of bioerodible implants implantable in a posterior ocular region, each implant comprising (i) an anti-inflammatory drug, and; (ii) a bioerodible polymer, wherein the plurality of bioerodible implants can substantially continuously release the drug for a period of between 5 days and 1 year.

A preferred method for making an extended release bioerodible implant for treating an ocular condition can be by: (a) blending and extruding an active agent and a first bioerodible polymer to form a first solid material; (b) breaking the first solid material into particles; (c) blending and extruding (or direct compressing) the particles with the active agent with a second bioerodible polymer, to thereby form a bioerodible implant, wherein the bioerodible implant can release a therapeutic level of the active agent at a substantially continuous rate for a period time between about 50 days and about 1 year.

In another embodiment a bioerodible implant for treating a ocular condition, the bioerodible implant can be made by: (a) blending (followed by extruding, injection molding or the like) a steroidal anti-inflammatory drug and a first bioerodible polymer to form a first solid material; (b) breaking the solid material into particles; (c) blending (followed by extruding, injection molding or the like) the particles with the steroidal anti-inflammatory drug and a second bioerodible polymer to form a bioerodible implant, wherein the bioerodible implant can release a therapeutic level of the active agent at a substantially continuous rate for a period time between about 50 days and about 1 year. Such a bioerodible implant can substantially continuously release the drug.

A bioerodible implant for treating a ocular condition can also be made as (a) a dispersion comprising an active agent dispersed with a first bioerodible polymer, (b) a particle comprising the active agent and a second bioerodible polymer, wherein the particle has an active agent release characteristic which differs from the active agent release characteristic of the dispersion.

A method for treating an ocular condition according to our invention can comprise implanting into an ocular region or site a drug delivery system set forth herein.

Therapeutic agents particularly useful for inclusion in an intraocular drug delivery system for administering to an intraocular location, such as an anterior sub-Tenon's area, include antihypertensive drugs such as brimonidine tartrate, brimonidine free base, latanoprost, bimatoprost and its analogues, beta blockers, carbonic anhydrase inhibitors, and prostaglandin receptor agonists including EP2 and EP4 E-compounds and timolol maleate. Additionally, the drug delivery system can comprise a glucocorticoid receptor blocker (such as RU-486) to help reduce corticosteroid induced ocular hypertension, as well as a sclera penetrant enhancer, such as BAK, as an excipient (especially advantageous in a sub-Tenon's implant) which acts to facilitate transit of the therapeutic agent through the sclera (i.e. by reducing the diffusion coefficient of the therapeutic agent).

An embodiment of our invention is a biocompatible, injectable intraocular drug delivery system comprising a plurality of microspheres, and an aqueous vehicle for the microspheres. The microspheres can consist essentially of a therapeutic agent which is an estradiol, and one or more biodegradable polymers, all of which biodegradable polymers are polylactic acid (PLA) polymers. This drug delivery system can have a viscosity which permits the drug delivery system to be injected into an intraocular location through an 18 to 30 or 20 to 28 gauge syringe needle. The estradiol in this drug delivery system can be a 2-methoxyestradiol. The estradiol in the drug delivery system can comprise from about 20 wt % to about 50 wt % of the weight of the microspheres and the PLA polymer comprises from about 50 wt % to about 80 wt % of the weight of the microspheres. The PLA polymer can be a poly(D,L)lactide polymer. Additionally, the PLA polymer can have an inherent viscosity of between about 1 dL/gm and about 1.4 dL/gm. Furthermore, the microspheres of this drug delivery system can have an average diameter between about 2 microns and about 6 microns.

A preferred embodiment of our invention is a biocompatible, injectable intraocular drug delivery system which comprises a plurality of microspheres with an average diameter between about 2 microns and about 6 microns, and an aqueous vehicle for the microspheres, wherein the microspheres consist essentially of: (1) a 2-methoxyestradiol, wherein the 2-methoxyestradiol comprises from about 20 wt % to about 50 wt % of the weight of the microspheres, and; (2) one or more biodegradable polymers, all of which biodegradable polymers are poly(D,L)lactide polymers with an inherent viscosity of between about 1 dL/gm and about 1.4 dL/gm, wherein the PLA polymer comprises from about 50 wt % to about 80 wt % of the weight of the microspheres, and; wherein the drug delivery system can be injected into an intraocular location through a 20 to 26 gauge syringe needle.

Our invention also encompasses a method for treating an ocular condition, the method comprising the steps of: (a) preparing a biocompatible drug delivery system comprising a plurality of microspheres, and an aqueous vehicle for the microspheres, wherein the microspheres consist essentially of a therapeutic agent which is an estradiol, and one or more biodegradable polymers, all of which biodegradable polymers are polylactic acid (PLA) polymers, and; (b) injecting the drug delivery system into an intraocular location through a 20 to 26 gauge syringe needle, thereby treating an ocular condition, wherein the method does not result in significant ocular surface hyperemia. In this method the intraocular location can be a sub-Tenon, subconjunctival or retrobulbar intraocular location.

Another embodiment of our invention is a biocompatible, injectable intraocular drug delivery system comprising a plurality of microspheres, and an aqueous vehicle for the microspheres, wherein the microspheres consist essentially of: (1) a therapeutic agent which is an alpha 2 adrenergic agonist, and; (2) one or more biodegradable polymers, all of which biodegradable polymers are polylactic acid (PLA) polymers, and; wherein the drug delivery system has a viscosity at 20°

C. of between about 15,000 cps and about 100,000 cps which permits the drug delivery system to be injected into an intraocular location through a 24 to 30 gauge syringe needle. The alpha 2 adrenergic agonist can be a brimonidine (as used herein the word "brimonidine" when used by itself includes brimonidine free base and/or brimonidine tartrate). Additionally, the alpha 2 adrenergic agonist can comprise from about 0.5 wt % to about 15 wt % of the microspheres and the PLA polymer comprises from about 85 wt % to about 99.5 wt % of the microspheres and the microspheres can have an average diameter between about 8 microns and about 14 microns. Significantly, the microspheres can release between about 0.5 μg/day to about 40 μg/day of the alpha 2 adrenergic agonist over a period of time of between about 10 days and about 100 days.

Another preferred embodiment of our invention is a biocompatible, injectable intraocular drug delivery system comprising (a) a plurality of microspheres with an average diameter between about 8 microns and about 14 microns, and (b) an aqueous vehicle for the microspheres, wherein the microspheres consist essentially of: (1) a brimonidine, wherein the brimonidine comprises from about 0.5 wt % to about 15 wt % of the microspheres, and; (2) one or more biodegradable polymers, all of which biodegradable polymers are poly(D, L)lactide polymers with an inherent viscosity of between about 0.4 dL/gm and about 0.8 dL/gm, wherein the PLA polymer comprises from about 85 wt % to about 99.5 wt % of the microspheres, and; wherein the drug delivery system can be injected into an intraocular location through a 20 to 26 gauge syringe needle and the microspheres can release between about 0.5 μg/day to about 20 μg/day of the brimonidine a period of time of between about 10 days and about 100 days.

Our invention also includes a method for treating an ocular condition, the method comprising the steps of: (a) preparing a biocompatible drug delivery system comprising a plurality of microspheres, and an aqueous vehicle for the microspheres, wherein the microspheres consist essentially of a therapeutic agent which is a brimonidine, and one or more biodegradable polymers, all of which biodegradable polymers are polylactic acid (PLA) polymers, and; (b) injecting the drug delivery system into an intraocular location through a 20 to 26 gauge syringe needle, thereby treating an ocular condition, wherein the method does not result in significant ocular surface hyperemia.

A preferred method within the scope of our invention is a method for treating an ocular condition, the method comprising the steps of: (a) preparing a biocompatible drug delivery system comprising an implant which consists essentially of an alpha 2 adrenergic agonist, and one or more biodegradable polymers, all of which biodegradable polymers are polylactic acid (PLA) polymers or polyortho esters, and; (b) implanting the drug delivery system into an intraocular location thereby treating an ocular condition, wherein the method does not result in significant ocular surface hyperemia. The intraocular location can be a sub-Tenon, subconjunctival, suprachoroidal, intrascleral or retrobulbar intraocular location.

Another preferred method within the scope of our invention is a method for treating an ocular condition, the method comprising the steps of: (a) preparing a biocompatible drug delivery system comprising a an implant which consist essentially of a prostaglandin analog and one or more biodegradable polymers, all of which biodegradable polymers are polylactic acid (PLA) polymers or polyortho esters, and; (b) implanting the drug delivery system into an intraocular location thereby treating an ocular condition, wherein the method does not result in significant ocular surface hyperemia.

Another preferred method within the scope of our invention is a method for treating an ocular condition, the method comprising the steps of: (a) preparing a biocompatible drug delivery system comprising a an implant which consists essentially of an alpha 2 adrenergic agonist, and one or more biodegradable polylactic acid (PLA) polymers, and; (b) implanting the drug delivery system into an intravitreal location thereby treating an ocular condition.

DRAWINGS

The following drawings illustrate aspects and features of our invention.

FIG. 1 is a graph which shows the IOP (intraocular pressure) in mm Hg on the Y axis versus time in days on the X axis for rabbits who had either three or six 400 μg brimonidine DDS (drug delivery system) rod shaped implants administered to an anterior sub-Tenon intraocular location. The first data point at the far left of FIG. 1 were obtained on day 0 (the day on which the DDS were administered to the rabbit eyes). The three graphs in FIG. 1 show the effect on IOP over time of sub-tenon placement of: (a) six implants which provided total of 2400 μg of brimonidine; (b) three implants which provided total of 1200 μg of brimonidine, and; (c) placement of placebo implants. The photograph inserted at the bottom left hand corner of FIG. 1 is of a rabbit eye on day 21, showing the absence of ocular surface hyperemia and the presence of three sub-tenon placed 400 μg brimonidine implants.

FIG. 2 is a graph which shows on the Y axis the IOP measured (in mm Hg) after a dog eye received anterior sub-tenon insertion of three 150 μg brimonidine PLA implants. IOP was measured relative to the zero or baseline IOP. Baseline IOP is the IOP as measured just before the three implants were administered to the dog eye. Days after implant insertion (on day 1) is shown on the X axis.

FIG. 3 is a graph which shows on the Y axis the IOP measured (in mm Hg) after a dog eye received anterior sub-tenon injection of a microsphere suspension which contained 600 μg of bimatoprost. IOP was measured relative to the zero or baseline IOP. Days after implant insertion (on day 1) is shown on the X axis.

DESCRIPTION

Figure 1:
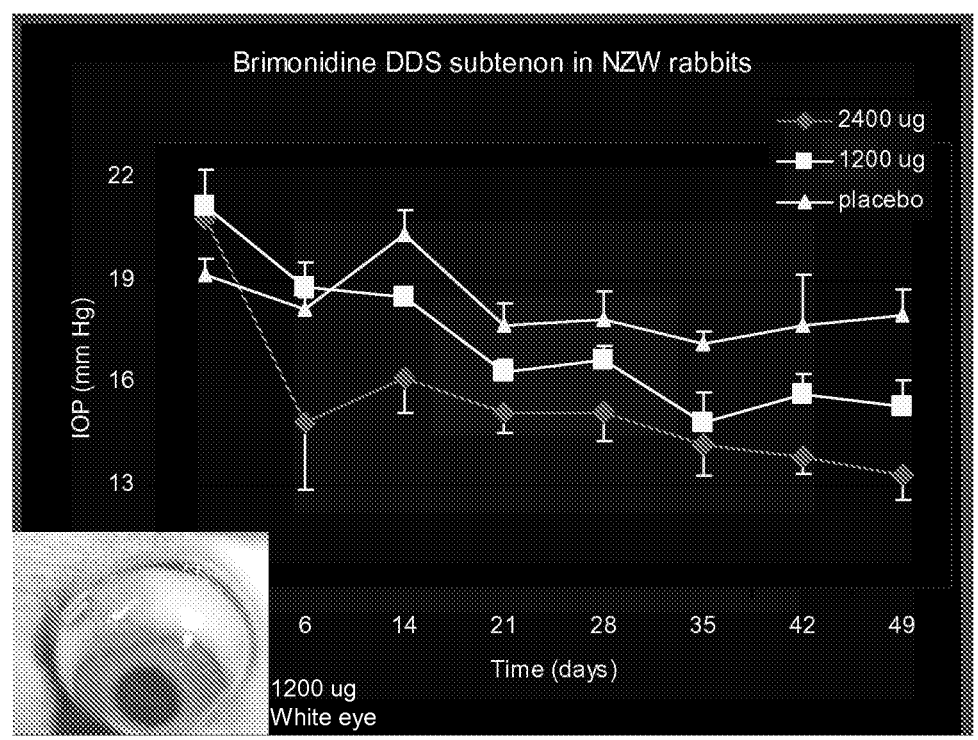

Our invention is based upon the discovery of particular drug delivery system formulations and methods for administering these drug delivery systems for treating various ocular conditions with little or no ocular surface hyperemia occurring after intraocular administration of the drug delivery systems as set forth herein. The present invention encompasses drug delivery systems which are structured and configured solely for intraocular, as opposed to topical or systemic, administration. The intraocular administration can be by implantation or injection. The drug delivery systems within the scope of our invention can be biodegradable implants and microspheres. The drug delivery systems can be monolithic, that is the active agent is homogenously distributed or dispersed throughout the biodegradable polymer matrix. The therapeutic agent can be released from drug delivery systems made according to the present invention for a period of time between about 20 days to 12 months or more. An important feature of our drug delivery systems is that they do not include any means (such as a cap, protrusion or suture tab) for fixing the drug delivery system to the intraocular location to which it is administered. Our drug delivery systems remain fixed in place with little risk of extrusion or migration because they are configured to conform to the curvature of the globe of the eye at the site of administration (i.e. by being in the form of a rod, wafer or disc) and have dimensions small enough to enable them to be placed intraocular (such as in a sub-tenon space or within the sclera) where they are bounded by surrounding ocular tissue.

Thus, the drug delivery systems disclosed herein are not sutured in place and do not have a cap, protrusion or other mechanism used to ensure a rigid fixation of the drug delivery system at the administration site. Suturing or other fixation means requires sensitive ocular tissues to be in contact with aspects of a drug delivery system which are not required in order to contain a therapeutic agent within or on the drug delivery system or to permit the therapeutic agent to be released in vivo. As such suturing or eye fixation means a merely peripheral or ancillary value and their use can increase healing time, patient discomfort and the risk of infection or other complications. Furthermore, sutures can create inflammation, and those that are not bioerodible, frequently require an additional procedure to remove the suture material.

The anterior sub-Tenon, anterior suprachoroidal space and anterior intrascleral locations extend from the corneal limbus (the location where the cornea meets the sclera) to approximately 2 mm to 10 mm posteriorly along the surface of the human eye. Further than about 10 mm from the corneal limbus one encounters posterior sub-Tenon, posterior suprachoroidal space and posterior intrascleral locations.

We have discovered that a anterior intraocular location administration of a drug delivery system, which is not sutured in place and does not comprise any particular fixation mechanism, advantageously places the drug delivery system at a location from which the drug delivery system is unlikely to extrude or migrate, and because of the anterior location also permits effective dosing of a hypertensive agent to the ciliary body and trabecular meshwork. Significantly, we have found that administration of a suitably configured drug delivery system to an anterior intraocular location using a suitable applicator for the drug delivery system provides a self-healing method, that is not only is suturing not required to retain the drug delivery system in place, nor is suturing (stitching) always required to close the wound at the site of entry to the intraocular administration site to permit it to heal. Self healing is accomplished through use of an biocompatible implant (not more than 12 mm in length) configured for intraocular administration through the canula of a 18-30 gauge needle.

We have found that when an intraocular drug delivery system is administered to an anterior sub-Tenon location in order to deliver a dose X of a therapeutic agent in order to achieve an antihypertensive therapeutic effect Y placement of the same drug delivery system at an anterior intrascleral location will require a dose of only about 0.5× of the therapeutic agent in order to achieve the same therapeutic effect Y, and placement of the same drug delivery system at a suprachoroidal location will require a dose of only about 0.3× to less than about 0.5× of the therapeutic agent in order to achieve the same therapeutic effect Y.

Thus, the deeper within the eye (as one proceeds from anterior sub-Tenon, to intrascleral, to suprachoroidal administration sites) a drug delivery system is administered in order to deliver an antihypertensive agent to an intraocular structure such as the ciliary body and/or the trabecular meshwork, a proportionally lower amount of the therapeutic agent is required to achieve the same antihypertensive effect with the same therapeutic agent.

Our invention requires an understanding of ocular morphology and structure. The exterior surface of the globe mammalian eye can have a layer of tissue known as Tenon's capsule, underneath which lies the sclera, followed by the choroid. Between Tenon's capsule and the sclera is a virtual space known as a sub-Tenon space. Another virtual space lies between the sclera and the choroid, referred to as the suprachoroidal space. Delivery of a therapeutic agent to an ocular location the front of the eye (such as the ciliary body) can be facilitated by placement of a suitably configured drug delivery system to a location such as the anterior sub-Tenon space, the anterior suprachoroidal space. Additionally, a drug delivery system can be administered within the sclera, for example to an anterior intrascleral location. Upon lateral movement of the therapeutic agent from such drug delivery implant locations it can diffuse or be transported through the conjunctiva and sclera to the cornea. Upon perpendicular movement of the therapeutic agent through the sclera and/or the choroid it can be delivered to anterior structures of the eye. For example, an aqueous humor suppressant for the treatment of ocular hypertension or glaucoma, can be delivered from drug delivery systems placed in the anterior sub-Tenon space, the suprachoroidal space or intrascleral to the region of the ciliary body.

As can be understood an intrascleral administration of a drug delivery system does not place the drug delivery system as close to the vitreous as does a suprachoroidal (between the sclera and the choroid) administration. For that reason an intrascleral administration of a drug delivery system can be preferred over a suprachoroidal administration so as to reduce the possibility of inadvertently accessing the vitreous upon administration of the drug delivery system.

Additionally, since the lymphatic network resides in or above the tenon's fascia of the eye and deeper ocular tissues have a reduced blood flow velocity, administration of a drug delivery system in a sub-tenon and more eye interior location can provide the dual advantages of avoiding the rapid removal of the therapeutic agent by the ocular lymphatic system (reduced lymphatic drainage) and the presence of only a low circulatory removal of the therapeutic agent from the administration site. Both factors favor passage of effective amounts of the therapeutic agent to the ciliary body and trabecular meshwork target tissue.

An important characteristic of a drug delivery system within the scope of our invention is that it can be implanted or injected into an intraocular location (such as an anterior sub-Tenon, subconjunctival or suprachoroidal location) to provide sustained release of a therapeutic agent without the occurrence of or the persistence of significant hyperemia at and adjacent to the site of the intraocular implantation or injection. This is a significant advantage of our drug delivery systems because hyperemia of ocular tissues indicates a toxicity and/or a lack of biocompatibility of one or more of the constituents of the drug delivery system implanted or injected. Additionally, hyperemia is a cosmetically undesirable side effect.

Table 2 below sets forth a visually determined yet quantitative method for determining and recording the extent of any ocular surface hyperemia (OSH) present after intraocular administration of a drug delivery system. Thus, the OSH can be evaluated daily according to the indicated pictorial eye surface factors. OSH correlates well to gross ocular irritation at the prior site of implantation or injection. The Table 2 OSH scoring system is useful for determination of the extent of hyperemia after a peripheral, anterior intraocular administration (such as to an anterior sub-Tenon space). A peripheral anterior intraocular administration excludes, for example, an intravitreal administration.

In a preferred embodiment of our invention ocular surface hyperemia (OSH) scores by or within tens days after intraocular administration are at or return to a normal or hi normal score, and this can be used as a definition of a not significant amount or occurrence of OSH. Preferably, the OSH score remains at normal or high normal for at least the next fifty days after intraocular administration of the drug delivery system.

TABLE 2

| Appearance | OSH Score |
| --- | --- |
| Normal: normal eye color | 0 |
| Hi-normal: slightly red eye, but predominantly normal appearance | +0.5 |
| Mild: number and diameter of red eye veins is greater than normal | +1 |
| Moderate: bright red eye veins, with increased number and diameter of vessels, deeper crimson red, | +2 |
| Severe: prominent beefy red eye veins accompanied by a reddish color of the conjunctiva | +3 |

Importantly, when a drug delivery system comprises a PLA and/or a PLGA polymer, the rate of PLA and/or PLGA polymer degradation in vivo determines the local lactic acid and glycolic acid concentrations present in the sub-Tenon space. We have discovered that preferential usage of PLA and PLGA polymers mixtures in the formulation of a drug delivery system intended for intraocular administration can provide a more neutral (and hence a more physiologic) pH environment. This can reduce the incidence of ocular hyperemia and also decrease the risk of ocular tissue toxicity due to an unfavorable local pH environment caused by in vivo DDS polymer bioerosion. We determined that because in the anterior sub-Tenon's space the buffering capacity of the ocular tissue therein is quite limited, a drug delivery system formulated of polymers or co-polymers that are predominantly PLA, with slow degradation rates can provide a DDS with the advantages of extended drug release, reduced or no hyperemia and little or no pH-induced ocular tissue toxicity.

Polylactide (PLA) polymers exist in 2 chemical forms, poly(L-lactide) and poly(D,L-lactide). The pure poly(L-lactide) is regioregular and therefore is also highly crystalline, therefore degrades in vivo at a very slow rate. The poly(D,L-lactide) is regiorandom which leads to more rapid degradation in vivo. Therefore a PLA polymer which is a mixture of predominantly poly(L-lactide) polymer, the remainder being a poly(D-lactide) polymer will degrade in vivo at a rate slower that a PLA polymer which is predominantly poly(D-lactide) polymer. A PLGA is a co-polymer that combines poly(D,L-lactide) with poly(glycolide) in various possible ratios. The higher the glycolide content in a PLGA the faster the polymer degradation.

In one embodiment of our invention, a drug delivery system for intraocular administration (i.e. by implantation in the sub-Tenon space) comprises configured, consists of, or consists essentially of at least a 75 weight percent of a PLA and no more than about a 25 weight percent of a poly(D,L-lactide-co-glycolide) polymer.

The ciliary body region does not show a rapid rate of drug clearance. Hence we postulate that a therapeutic agent administered by an intraocular administration, such as by a subconjunctival injection, at the equator of the eye can from that location enter the eye to reach the ciliary body region. We selected the anterior sub-Tenon space as a preferred location for administration of a drug delivery system because from this location a therapeutic agent released from a drug delivery system we would expect to diffuse to or be transported to the ciliary body region (the target tissue). In other words, administration of a drug delivery system to the anterior sub-Tenon space can efficiently deliver an aqueous humor (elevated IOP) suppressants to the ciliary body region to treat ocular conditions such as ocular hypertension and glaucoma. For the purpose of our invention we define the anterior sub-Tenon, anterior suprachoroidal space and anterior intrascleral locations to extend from the corneal limbus (the location where the cornea meets the sclera) to approximately 2 to 10 mm posteriorly along the surface of the human eye. The ideal destination for aqueous humor suppressants entering through this region is the nonpigmented ciliary epithelium where the aqueous humor in produced. Other tissues that would be accessed with a drug delivery system in an anterior intraocular (such as sub-Tenon's) location can be the ciliary body stroma, iris root, and the trabecular meshwork. Therapeutic agents which reduce intraocular pressure primarily by improving uveoscleral flow, such as the prostamides and prostaglandins, would be efficiently delivered with a delivery system in the anterior sub-Tenon's area.

Typically, what occurs with eye drops is the active agent goes through the cornea, is fairly equally distributed through the aqueous humor, goes through the trabecular meshwork and also into the ciliary body. This all occurs 360 degrees around the eye where the ciliary body (aqueous production area) and the trabecular meshwork & iris root (where drainage occurs). Surprisingly we have determined using drug diffusion MRI imaging studies that with sub-Tenon's implants in one quadrant of the eye, the active agent drug preferentially goes through the ciliary body region in the quadrant of the implant, then the active agent goes into the aqueous humor and is equally distributed, then the active agent exits with the normal pathways of drainage (trabecular meshwork & iris root) 360 degrees Therefore, an anterior sub-Tenon's implant placed in one quadrant, can distribute active agent 360 degrees in the anterior segment.

Preferred drug delivery systems are sustained-release implants or microspheres. The implants in the anterior sub-Tenon's location preferably have a low profile, that is are less than 1 mm in thickness, and more preferably is less than 0.5 mm in diameter, to thereby reduce the chance of implant extrusion and to also limit the foreign body sensation. In the adult human, the ciliary body extends 1 to 3 mm behind the corneal limbus; therefore the ideal location of the drug delivery system would 2 to 6 mm behind the limbus. Any location 360 degrees around the eye for anterior sub-Tenon's placement is permissible with the caveat that a location under the eyelid may be preferred to make the delivery system less visually apparent by others. Drug delivery systems within the scope of our invention can be placed anteriorly in the eye over the ciliary body region with an intrascleral, suprachoroidal, or intravitreal location.

Within the scope of our invention are suspensions of microspheres which can be administered to an intraocular location through a syringe needle. Administration of such a suspension requires that the viscosity of the microsphere suspension at 20° C. be less than about 300,000 cP. The viscosity of water at 20° C. is 1.002 cP (cP is centiposie, a measure of viscosity). The viscosity of olive oil is 84 cP, of castor oil 986 P and of glycerol 1490 cP The implants of our invention can include a therapeutic agent mixed with or dispersed within a biodegradable polymer. The implant compositions can vary according to the preferred drug release profile, the particular active agent used, the ocular condition being treated, and the medical history of the patient. Therapeutic agents which can be used in our drug delivery systems include, but are not limited to (either by itself in a drug delivery system within the scope of the present invention or in combination with another therapeutic agent): ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciprofloxin, etc.; sulfonamides such as chloramine T; and sulfones such as sulfanilic acid as the hydrophilic entity, anti-viral drugs, e.g. acyclovir, gancyclovir, vidarabine, azidothymidine, azathioprine, dideoxyinosine, dideoxycytosine, dexamethasone, ciprofloxin, water soluble antibiotics, such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, keterolac, naproxen, etc., an anesthetic, e.g. lidocaine; beta.-adrenergic blocker or beta.-adrenergic agonist, e.g. ephidrine, epinephrine, etc.; aldose reductase inhibitor, e.g. epalrestat, ponalrestat, sorbinil, tolrestat; antiallergic, e.g. cromolyn, beclomethasone, dexamethasone, and flunisolide; colchicine, anihelminthic agents, e.g. ivermectin and suramin sodium; antiamebic agents, e.g. chloroquine and chlortetracycline; and antifungal agents, e.g. amphotericin, etc., antiangiogenesis compounds such as anecortave acetate, retinoids such as Tazarotene, anti-glaucoma agents, such as brimonidine (Alphagan and Alphagan P), acetozolamide, bimatoprost (Lumigan), timolol, mebefunolol; memantine, latanoprost (Xalatan); alpha-2 adrenergic receptor agonists; 2-methoxyestradiol; anti-neoplastics, such as vinblastine, vincristine, interferons; alpha, beta and gamma, antimetabolites, such as folic acid analogs, purine analogs, and pyrimidine analogs; immunosuppressants such as azathiprine, cyclosporine and mizoribine; miotic agents, such as carbachol, mydriatic agents such as atropine, protease inhibitors such as aprotinin, camostat, gabexate, vasodilators such as bradykinin, and various growth factors, such epidermal growth factor, basic fibroblast growth factor, nerve growth factors, carbonic anhydrase inhibitors, and the like.

In one variation the active agent is methotrexate. In another variation, the active agent is a retinoic acid. In another variation, the active agent is an anti-inflammatory agent such as a nonsteroidal anti-inflammatory agent. Nonsteroidal anti-inflammatory agents that may be used include, but are not limited to, aspirin, diclofenac, flurbiprofen, ibuprofen, ketorolac, naproxen, and suprofen. In a further variation, the anti-inflammatory agent is a steroidal anti-inflammatory agent, such as dexamethasone.

Steroidal anti-inflammatory agents that can be used in our drug delivery systems can include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In one embodiment, cortisone, dexamethasone, fluocinolone, hydrocortisone, methylprednisolone, prednisolone, prednisone, and triamcinolone, and their derivatives, are preferred steroidal anti-inflammatory agents. In another preferred variation, the steroidal anti-inflammatory agent is dexamethasone. In another variation, the biodegradable implant includes a combination of two or more steroidal anti-inflammatory agents.

The active agent, such as a steroidal anti-inflammatory agent, can comprise from about 10% to about 90% by weight of the implant. In one variation, the agent is from about 40% to about 80% by weight of the implant. In a preferred variation, the agent comprises about 60% by weight of the implant. In a more preferred embodiment of the present invention, the agent can comprise about 50% by weight of the implant.

The therapeutic active agent present in our drug delivery systems can be homogeneously dispersed in the biodegradable polymer of the implant or microspheres. The implant can be made, for example, by a sequential or double extrusion method. The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the active agent of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the implant.

Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked. If crosslinked, they are usually not more than lightly crosslinked, and are less than 5% crosslinked, usually less than 1% crosslinked.

For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen can be present as amide, cyano, and amino. An exemplary list of biodegradable polymers that can be used are described in Heller, *Biodegradable Polymers in Controlled Drug Delivery*, In: "CRC Critical Reviews in Therapeutic Drug Carrier Systems", Vol. 1. CRC Press, Boca Raton, Fla. (1987).

Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In certain variations, 25/75 PLGA and/or 50/50 PLGA copolymers are used. In other variations, PLGA copolymers are used in conjunction with polylactide polymers.

Biodegradable polymer matrices that include mixtures of hydrophilic and hydrophobic ended PLGA may also be employed, and are useful in modulating polymer matrix degradation rates. Hydrophobic ended (also referred to as capped or end-capped) PLGA has an ester linkage hydrophobic in nature at the polymer terminus. Typical hydrophobic end groups include, but are not limited to alkyl esters and aromatic esters. Hydrophilic ended (also referred to as uncapped) PLGA has an end group hydrophilic in nature at the polymer terminus. PLGA with a hydrophilic end groups at the polymer terminus degrades faster than hydrophobic ended PLGA because it takes up water and undergoes hydrolysis at a faster rate (Tracy et al., *Biomaterials* 20:1057-1062 (1999)). Examples of suitable hydrophilic end groups that may be incorporated to enhance hydrolysis include, but are not limited to, carboxyl, hydroxyl, and polyethylene glycol. The specific end group will typically result from the initiator employed in the polymerization process. For example, if the initiator is water or carboxylic acid, the resulting end groups will be carboxyl and hydroxyl. Similarly, if the initiator is a monofunctional alcohol, the resulting end groups will be ester or hydroxyl.

Other agents may be employed in a drug delivery system formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

The biodegradable drug delivery systems can also include additional hydrophilic or hydrophobic compounds that accelerate or retard release of the active agent. Additionally, release modulators such as those described in U.S. Pat. No. 5,869,079 can be included in the implants. The amount of release modulator employed will be dependent on the desired release profile, the activity of the modulator, and on the release profile of the glucocorticoid in the absence of modulator. Where the buffering agent or release enhancer or modulator is hydrophilic, it may also act as a release accelerator. Hydrophilic additives act to increase the release rates through faster dissolution of the material surrounding the drug particles, which increases the surface area of the drug exposed, thereby increasing the rate of drug diffusion. Similarly, a hydrophobic buffering agent or enhancer or modulator can dissolve more slowly, slowing the exposure of drug particles, and thereby slowing the rate of drug diffusion.

A drug delivery system within the scope of the present invention can be formulated with particles of an active agent dispersed within a biodegradable polymer matrix. Without being bound by theory, it is believed that the release of the active agent can be achieved by erosion of the biodegradable polymer matrix and by diffusion of the particulate agent into an ocular fluid, e.g., the vitreous, with subsequent dissolution of the polymer matrix and release of the active agent. Factors which influence the release kinetics of active agent from the implant can include such characteristics as the size and shape of the implant, the size of the active agent particles, the solubility of the active agent, the ratio of active agent to polymer(s), the method of manufacture, the surface area exposed, and the erosion rate of the polymer(s). The release kinetics achieved by this form of active agent release are different than that achieved through formulations which release active agents through polymer swelling, such as with crosslinked hydrogels. In that case, the active agent is not released through polymer erosion, but through polymer swelling and drug diffusion, which releases agent as liquid diffuses through the pathways exposed.

The release rate of the active agent can depend at least in part on the rate of degradation of the polymer backbone component or components making up the biodegradable polymer matrix. For example, condensation polymers may be degraded by hydrolysis (among other mechanisms) and therefore any change in the composition of the implant that enhances water uptake by the implant will likely increase the rate of hydrolysis, thereby increasing the rate of polymer degradation and erosion, and thus increasing the rate of active agent release.

The release kinetics of the implants of the present invention can be dependent in part on the surface area of the implants. A larger surface area exposes more polymer and active agent to ocular fluid, causing faster erosion of the polymer matrix and dissolution of the active agent particles in the fluid. Therefore, the size and shape of the implant may also be used to control the rate of release, period of treatment, and active agent concentration at the site of implantation. At equal active agent loads, larger implants will deliver a proportionately larger dose, but depending on the surface to mass ratio, may possess a slower release rate. For implantation in an ocular region, the total weight of the implant preferably ranges, e.g., from about 100 µg to about 15 mg. More preferably, from about 300 µg to about 10 mg, and most preferably from about 500 µg to about 5 mg. In a particularly preferred embodiment of the present invention the weight of an implant is between about 500 µg and about 2 mg, such as between about 500 µg and about 1 mg.

The bioerodible implants are typically solid, and may be formed as particles, sheets, patches, plaques, films, discs, fibers, rods, and the like, or may be of any size or shape compatible with the selected site of implantation, as long as the implants have the desired release kinetics and deliver an amount of active agent that is therapeutic for the intended medical condition of the eye. The upper limit for the implant size will be determined by factors such as the desired release kinetics, toleration for the implant at the site of implantation, size limitations on insertion, and ease of handling. For example, the vitreous chamber is able to accommodate relatively large rod-shaped implants, generally having diameters of about 0.05 mm to 3 mm and a length of about 0.5 to about 10 mm. In one variation, the rods have diameters of about 0.1 mm to about 1 mm. In another variation, the rods have diameters of about 0.3 mm to about 0.75 mm. In yet a further variation, other implants having variable geometries but approximately similar volumes may also be used.

The proportions of active agent, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the drug delivery device is added to a measured volume of a solution containing 0.9% NaCl in water, where the solution volume will be such that the drug concentration after release is less than 20%, and preferably less than 5%, of saturation. The mixture is maintained at 37° C. and stirred slowly to ensure drug diffusion after bioerosion. The appearance of the dissolved drug as a function of time may be followed by various methods known in the art, such as spectrophotometrically, HPLC, mass spectroscopy, etc.

Examples of ocular conditions which can be treated by the drug delivery systems and methods of the invention include, but are not limited to, glaucoma, uveitis, macular edema, macular degeneration, retinal detachment, posterior ocular tumors, fungal or viral infections, multifocal choroiditis, diabetic retinopathy, proliferative vitreoretinopathy (PVR), sympathetic opthalmia, Vogt Koyanagi-Harada (VKH) syndrome, histoplasmosis, uveal diffusion, and vascular occlusion. In one variation, the implants are particularly useful in treating such medical conditions as uveitis, macular edema, vascular occlusive conditions, proliferative vitreoretinopathy (PVR), and various other retinopathies.

The drug delivery systems of our invention can be injected to an intraocular location by syringe or can be inserted (implanted) into the eye by a variety of methods, including placement by forceps, by trocar, or by other types of applicators, after making an incision in the sclera. In some instances, a trocar or applicator may be used without creating an incision. In a preferred variation, a hand held applicator is used to insert one or more biodegradable implants into the eye. The hand held applicator typically comprises an 18-30 GA stainless steel needle, a lever, an actuator, and a plunger. Suitable devices for inserting an implant or implants into a posterior ocular region or site includes those disclosed in U.S. patent application Ser. No. 10/666,872.

The method of implantation generally first involves accessing the target area within the ocular region with the needle, trocar or implantation device. Once within the target area, e.g., the vitreous cavity, a lever on a hand held device can be depressed to cause an actuator to drive a plunger forward. As the plunger moves forward, it can push the implant or implants into the target area (i.e. the vitreous).

Various techniques may be employed to make implants within the scope of the present invention. Useful techniques include phase separation methods, interfacial methods, extrusion methods, compression methods, molding methods, injection molding methods, heat press methods and the like.

Choice of the technique, and manipulation of the technique parameters employed to produce the implants can influence the release rates of the drug. Room temperature compression methods result in an implant with discrete microparticles of drug and polymer interspersed. Extrusion methods result in implants with a progressively more homogenous dispersion of the drug within a continuous polymer matrix, as the production temperature is increased.

The use of extrusion methods allows for large-scale manufacture of implants and results in implants with a homogeneous dispersion of the drug within the polymer matrix. When using extrusion methods, the polymers and active agents that are chosen are stable at temperatures required for manufacturing, usually at least about 50° C. Extrusion methods use temperatures of about 25° C. to about 150° C., more preferably about 60° C. to about 130° C.

Different extrusion methods may yield implants with different characteristics, including but not limited to the homogeneity of the dispersion of the active agent within the polymer matrix. For example, using a piston extruder, a single screw extruder, and a twin screw extruder will generally produce implants with progressively more homogeneous dispersion of the active. When using one extrusion method, extrusion parameters such as temperature, extrusion speed, die geometry, and die surface finish will have an effect on the release profile of the implants produced.

In one variation of producing implants by a piston extrusion methods, the drug and polymer are first mixed at room temperature and then heated to a temperature range of about 60° C. to about 150° C., more usually to about 100° C. for a time period of about 0 to about 1 hour, more usually from about 0 to about 30 minutes, more usually still from about 5 minutes to about 15 minutes, and most usually for about 10 minutes. The implants are then extruded at a temperature of about 60° C. to about 130° C., preferably at a temperature of about 90° C.

In an exemplary screw extrusion method, the powder blend of active agent and polymer is added to a single or twin screw extruder preset at a temperature of about 80° C. to about 130° C., and directly extruded as a filament or rod with minimal residence time in the extruder. The extruded filament or rod is then cut into small implants having the loading dose of active agent appropriate to treat the medical condition of its intended use.

Implant systems according to the invention can include a combination of a number of bioerodible implants, each having unique polymer compositions and drug release profiles that when co-administered provide for an extended continuous release of drug. Further, the achieved continuous release of drug is both prolonged and distinct from the release profile that would occur with a single implant consisting of a blend of the polymers. For example, to achieve continuous release of at least 120 days, three individual implants made of separate polymers that have fast, medium and slow release characteristics can be employed, with the fast release implant releasing most of the drug from 0-60 days, the medium release implant releasing most of the drug from 60-100 days, and the slow release implant releasing most of the drug from 100 days on. Examples of fast release implants include those made of certain lower molecular weight, fast degradation profile polylactide polymers, such as R104 made by Boehringer Ingelheim GmbH, Germany, which is a poly(D,L-lactide) with a molecular weight of about 3,500. Examples of medium release implants include those made of certain medium molecular weight, intermediate degradation profile PLGA co-polymers, such as RG755 made by Boehringer Ingelheim GmbH, Germany, which is a poly(D,L-lactide-co-glycolide with wt/wt 75% lactide:25% glycolide, a molecular weight of about 40,000 and an inherent viscosity of 0.50 to 0.70 dl/g. Examples of slow release implants include those made of certain other high molecular weight, slower degradation profile polylactide polymers, such as R203/RG755 made by Boehringer Ingelheim GmbH, Germany, for which the molecular weight is about 14,000 for R203 (inherent viscosity of 0.25 to 0.35 dl/g) and about 40,000 for RG755. When administered together, these implants provide for an extend continuous release of drug over a period of at least 120 days in vitro which can result in sustained drug levels (concentration) of at least about 5-10 ng dexamethasone equivalent/mL in the vitreous (i.e. in vivo) for up to about 240 days.

Single bioerodible implants with extended release profiles can also be prepared according to the invention using two or more different bioerodible polymers each having different release characteristics. In one such method, particles of a drug or active agent are blended with a first polymer and extruded to form a filament or rod. This filament or rod is then itself broken first into small pieces and then further ground into particles with a size (diameter) between about 30 µm and about 50 µm. which are then blended with an additional quantities of the drug or active agent and a second polymer. This second mixture is then extruded into filaments or rods which are then cut to the appropriate size to form the final implant. The resultant implant has a release profile different than that of an implant created by initially blending the two polymers together and then extruding it. It is posited that formed implant includes initial particles of the drug and first polymer having certain specific release characteristics bound up in the second polymer and drug blend that itself has specific release characteristics that are distinct from the first. Examples of implants include those formed with RG755, R203, RG503, RG502, RG 502H as the first polymer, and RG502, RG 502H as the second polymer. Other polymers that can be used include PDL (poly(D,L-lactide)) and PDLG (poly(D,L-lactide-co-glycolide)) polymers available from PURAC America, Inc. Lincolnshire, Ill. Poly(caprolactone) polymers can also be used. The characteristics of the specified polymers are (1) RG755 has a molecular weight of about 40,000, a lactide content (by weight) of 75%, and a glycolide content (by weight) of 25%; (2) R203 has a molecular weight of about 14,000, and a lactide content of 100%; (3) RG503 has a molecular weight of about 28,000, a lactide content of 50%, and a glycolide content of 50%; (4) RG502 has a molecular weight of about 11,700 (inherent viscosity of 0.16 to 0.24 dl/g), a lactide content of 50%, and a glycolide content of 50%, and; (5) RG502H has a molecular weight of about 8,500, a lactide content of 50%, a glycolide content of 50% and free acid at the end of polymer chain.

Generally, if inherent viscosity is 0.16 the molecular weight is about 6,300, and if the inherent viscosity is 0.28 the molecular weight is about 20,700. It is important to note that all polymer molecular weights set forth herein are averaged molecular weights in Daltons.

According to our invention continual or substantially continual release of drug at levels corresponding to at least 10 ng/ml of dexamethasone or dexamethasone equivalent for at least 60 days can be achieved.

In other methods, single implants can be made using polymers with differing release characteristics where separate drug-polymer blends are prepared that are then co-extruded to create implants that contain different areas or regions having different release profiles. The overall drug release profile of these co-extruded implants are different than that of an implant created by initially blending the polymers together and then extruding them. For example, first and second blends of drug or active agent can be created with different polymers and the two blends can be co-axially extruded to create an implant with an inner core region having certain release characteristics and an outer shell region having second, differing release characteristics.

The drug delivery systems disclosed herein can be used to prevent or to treat various ocular diseases or conditions, including the following: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

EXAMPLES

The following examples illustrate aspects and embodiments of our invention.

Example 1

2-Methoxyestradiol Polylactic Acid Microspheres (Rabbits)

In this experiment PLA-based microspheres comprising as active agent 2-methoxyestradiol were made and administered by injection into various intraocular locations of rabbit eyes. Significantly, we found that the microspheres were well tolerated and all eye redness (ocular surface hyperemia) was gone (resolved) within one-week after the intraocular administration. Hence, administration of these microspheres by the method set forth herein did not result in significant ocular surface hyperemia.

The microspheres used in this experiment comprised 29.7 weight % 2-methoxyestradiol as the therapeutic agent and 70.3 wt % poly(D,L)lactide polymer (Birmingham) with an inherent viscosity (iv) of 1.2 dL/gm. Prior to administration the microspheres were suspended in isotonic phosphate buffered saline (IPBS) pH 7.4, as the vehicle for the microspheres. A 200 µL volume of this microsphere suspension comprised 100 mg of microspheres per mL vehicle. The microspheres had an average diameter of about 4 µm and were made by solvent evaporation from methylene chloride into a polyvinyl acid (PVA) solution.

This was a three month study which used sixty female New Zealand White rabbits. Subconjunctival, sub-Tenon, and retrobulbar injections were carried out of the 2-methoxyestradiol formulated in 10% polylactic acid (PLA) microsphere (formulation 1) or as a 10% suspension of the 2-methoxyestradiol in 2% hydroxypropyl cellulose (HPC) (formulation 2). The sixty rabbits were divided into six groups of ten animals each. Each of the six groups received a single bilateral subconjunctival, sub-Tenon or retrobulbar injection of either 200 µL of PLA microsphere containing 5.96 mg of 2-methoxyestradiol, or 200 µL of a HPC suspension containing 20 mg of 2-methoxyestradiol.

The 10% PLA microsphere 2-methoxyestradiol formulation was delivered to the subconjunctiva by syringe using a 26-gauge needle, to the sub-Tenon intraocular location using a 23-gauge needle, and to the retrobulbar intraocular location using a 22-gauge needle. The 10% 2-methoxyestradiol in 2% HPC formulation was delivered using a 23-gauge needle for subconjunctival injection and a 21-gauge needle for sub-Tenon's administration.

Details of the six animal groups established and microspheres administrations are set forth in Table 3 below. At designated time points following dosing, blood and selected ocular tissues were collected.

TABLE 3

| Group | Number of Rabbits | Dose Route[a] | Formulation of 2-methoxyestradiol[b] | Target Dose Volume (µL/eye) | Collection Time[c] (Postdose) |
|---|---|---|---|---|---|
| 1 | 10 | Subconjunctival | 1 | 200 | 1 week, 2 weeks, 4 weeks, 8 weeks, 12 weeks |
| 2 | 10 | Sub-Tenon's | 1 | 200 | 1 week, 2 weeks, 4 weeks, 8 weeks, 12 weeks |
| 3 | 10 | Retrobulbar | 1 | 200 | 1 week, 2 weeks, 4 weeks, 8 weeks, 12 weeks |
| 4 | 10 | Subconjunctival | 2 | 200 | 1 week, 2 weeks, 4 weeks, 8 weeks, 12 weeks |
| 5 | 10 | Sub-Tenon's | 2 | 200 | 1 week, 2 weeks, 4 weeks, 8 weeks, 12 weeks |
| 6 | 10 | Retrobulbar | 2 | 200 | 1 week, 2 weeks, 4 weeks, 8 weeks, 12 weeks |

[a]Both eyes of each animal were dosed.
[b]Formulation No. 1 was 10% 2-methoxyestradiol PLA microsphere (100 mg/mL) in isotonic phosphate buffered saline (5.96 mg 2-methoxyestradiol/injection). Formulation No. 2 was 10% 2-methoxyestradiol (100 mg/mL) in 2% HPC (20 mg 2-methoxyestradiol/injection).
[c]Samples were collected from 2 animals/group/time point.

Formulation No. 1, (administered to Groups 1, 2 and 3), was a 10% suspension of 2-methoxyestradiol PLA microspheres prepared by adding thirteen mL of sterile isotonic phosphate-buffered saline (IPBS) with 1.3 g of 2-methoxyestradiol (PLA microsphere). The preparation was sonicated for 5 minutes, then vortex mixed for another 5 minutes to produce the appropriate suspension. Prior to dose and following administration, single 30-µL aliquots were obtained under sterile conditions. The density of the IPBS vehicle used was 1.0016 g/mL. Formulation No. 2 was sonicated for 5 minutes, then vortex mixed for another 5 minutes to produce the appropriate suspension. Prior to and following dose administration, single 30-µL aliquots were again obtained under sterile conditions.

Animals in Groups 1 and 4 were dosed by subconjunctival injection, the animals in Groups 2 and 5 were dosed by sub-Tenon's injection, while the animals in and Groups 3 and 6 were dosed by retrobulbar injection. Each animal was dosed in both eyes and received a dose of 200 µL/eye.

Immediately prior to dosing, the animals were lightly anesthetized with an intramuscular (IM) injection of xylazine (20 mg/mL) followed by an IM injection of ketamine (100 mg/mL). Eyes were prepared for dose administration as follows: Approximately 10 to 15 minutes prior to dose administration, two drops of 0.5% proparacaine hydrochloride were placed into each eye. Each eye was then rinsed for approximately 2 to 3 minutes with a diluted Betadine® solution prepared with 0.9% sodium chloride for injection, USP (providing 1% povidone iodine), made fresh each day of dosing. During this time, two cotton-tipped applicators (CTA), wetted with the povidone iodine solution, were used to clean the periorbital region including the eyelids and lid margins. A separate, clean CTA wetted with the iodine solution was used to clean the sclera and conjunctival sac formices, paying particular attention to the site of injection. The head was tipped laterally and the eyes were irrigated with 0.9% sterile saline using a syringe and catheter tip. One to two drops of 0.5% proparacaine hydrochloride (topical ophthalmic anesthetic) were applied to the eye.

Subconjunctival Periocular Injection (Groups 1 and 4)

The bulbar conjunctiva in the superior-temporal quadrant was elevated using forceps. A 26-gauge, ½-inch hypodermic needle, with the bevel facing upward, was inserted into the subconjunctival space and 0.2 mL of Formulation No. 1 (Group 1) or Formulation No. 2 (Group 4) was injected.

Sub-Tenon's Injection (Groups 2 and 5)

The sub-Tenon's injection was made by inserting a 25-gauge, ⅝-inch hypodermic needle, with the bevel facing upwards, through the bulbar conjunctiva (2 to 3 mm above the corneal limbus) and Tenon's capsule in the superior temporal quadrant beginning 2 to 3 mm from the limbus. A small bleb was made at this location by injecting 5 to 10 µL of sterile saline. The bleb of tissue was punctured with a 21-gauge, 1-inch, hypodermic needle to allow insertion of a blunt cannula into the sub-Tenon's space. A 23-gauge blunt cannula was inserted into the sub-Tenon's space and advanced in a posterior manner approximately 10 to 15 mm in a superior temporal direction. Then 0.2 mL of Formulation No. 1 (Group 2) or Formulation No. 2 (Group 5) was injected such that the microsphere suspension bolus was generally positioned in the posterior surface of the sclera near the optic nerve.

Retrobulbar Injection (Groups 3 and 6)

The retrobulbar injection was made using a 22-gauge, 1.5-inch spinal needle that was curved to follow the curve of the orbit from anterior to posterior. The needle was inserted at the conjunctival junction of the lateral canthus and the needle advanced posteriorly until the needle encountered the orbital bone at the posterior portion of the globe. The stylet was removed and aspiration was performed. If blood was aspirated, the needle was repositioned and the aspiration performed a second time. If blood was not aspirated, 0.2 mL of Formulation No. 1 (Group 3) or Formulation No. 2 (Group 6) was injected and the needle was removed. Following dose administration of each animal in Groups 1 thorough 6, AKWA Tears®, a bland ophthalmic ointment, was applied to the dosed eyes of each animal to prevent the eyes from drying out. In all Groups ciprofloxacin ointment was administered after dosing.

In this experiment we determined that particular formulations of 2-methoxyestradiol poly lactic acid polymer microspheres as a 10% suspension and 2% HPC formulations can be administered to various intraocular locations using a syringe. Significantly, at each of the three different sites of intra ocular administration with the formulations used only transient ocular irritation (ocular surface hyperemia) resulted and the hyperemia resolved (the surface of the eye returned to its normal white appearance at the site of the 2-methoxyestradiol administration) within the first week after dosing. No mortality or drug-related effects on body weight were observed.

Example 2

Subconjunctival Brimonidine Polylactic Acid Microspheres (Rabbits)

Two experiments were carried out in which lactic acid polymer, brimonidine therapeutic agent microspheres were made and injected by syringe into the subconjunctival space of rabbit eyes. The PLA brimonidine microspheres were injected as a suspension in an aqueous vehicle, such as isotonic phosphate buffered saline. The viscosity of the microsphere suspension at 20° C. was up to about 200,000 cps. The brimonidine containing microspheres were subconjunctivally injected (using a syringe needle gauge of 25-30) to provide therapeutic levels of the therapeutic agent (brimonidine) to the anterior chamber of the eye (for example to treat an elevated intraocular pressure) and/or to the posterior chamber of the eye to treat a retinal condition.

Significantly, in both experiments the brimonidine containing PLA microspheres were well tolerated (no hyperemia seven days after injection of the microspheres).

I. In a first experiment the formulation of the microspheres was 2 wt % brimonidine free base and 98 wt % PLA with an i.v. of 0.6 dL/gm (Birmingham Polymers), in IPBS vehicle at pH 7.4. The microspheres had an average diameter of 11 µm.

The microspheres were made by a solvent evaporation method from methylene chloride into a PVA (polyvinyl alcohol) solution. There were 10 to 100 mg/mL of the microsphere suspended in the IPBS vehicle. From 100 to 200 µL of the microsphere suspension was administered to the intraocular location.

The brimonidine free base microspheres with the brimonidine homogenously distributed or dispersed throughout the polylactic acid (PLA) were manufactured using an emulsion/solvent evaporation technique. The non-solvent (continuous aqueous phase) was saturated with brimonidine to prevent loss of brimonidine from the polymer phase and increase loading efficiency. Additionally, brimonidine saturated methanol was used to quench the emulsion. The methanol served as a sink to remove the dichloromethane quickly, hardening the microspheres before brimonidine can diffuse out of them. The detailed procedure used to make the microspheres is as follows:

1 gm of PLA was combined with 175 mg of brimonidine free base and mixed at 100° C. The PLA polymer/brimonidine mixture was then added to 60 milliliters of dichloromethane (polymer phase) at 38° C. 9.6 grams of PVA was combined with 80 mg of brimonidine free base in 320 milliliters of water at pH 7.8 to form an aqueous phase saturated with the free base (aqueous phase). The PLA polymer phase was emulsified with the aqueous phase by drop wise addition of the polymer phase into the aqueous phase under continuous mixing with a high shear impeller. 350 milliliters of methanol containing 900 mg of brimonidine free base was added to the emulsion and stirred for 4 hours to pull the dichloromethane out and harden the microspheres. The resulting PLA microspheres were further hardened by evaporation under vacuum for 1 hour. The hardened microspheres were separated from the remaining PVA solution by centrifugation. The microsphere pellets were suspended and washed 3 times with acetate buffer. The microspheres were dried under vacuum at 45° C. overnight. The dried microspheres were sized through sieves. The percent of brimonidine free base loaded into the microspheres was analyzed by UV and in both experiments intraocular pressure (IOP) was measured using a Medtronic Solan, Model 30 classic pneumatonometer.

II. In a second experiment New Zealand white rabbits received a single bilateral subconjunctival injection of microspheres made by a solvent evaporation process consisted of 98 wt % PLA (resomer 206) and 2 wt % brimonidine tartrate. The PLA resomer 206 has an inherent viscosity of 0.6 dL/gm. The microspheres were administered as a single 100 µL intraocular injection of brimonidine tartrate microsphere suspended in IPBS as vehicle. The microspheres were present in the formulation at a concentration of 10 mg/mL microsphere, so that the 100 µL injected comprised 980 µg of the PLA and 20 µg of the brimonidine tartrate.

The same microspheres (98 wt % PLA and 2 wt % brimonidine tartrate) were also formulated in the IPBS at a concentration of 200 mg/mL, so that with a 200 µL injection 9.8 mg of PLA and 200 µg of the brimonidine was administered. Placebos microspheres made contained 100 wt % PLA (10 mg/mL) or 100 wt % PLA 100 mg/mL. The sustained release of brimonidine from the injected microsphere was observed over a three month period after administration.

The female New Zealand White rabbits used in this experiment were 7-10 months old and weighed 2.49-3.36 kg on the day of dosing. The study carried out was a single injection parallel design, with 10 treatment groups and non-serial samples collected from each animal. Further details of the study are outlined in Table 4 below.

TABLE 4

| Group | Number of Rabbits | Treatment[a] (Day 1) | brimonidine tartrate Dosed | Euthanasia and Necropsy (Day After Dosing) | Ophthalmic Observation (Day After Dosing) |
|---|---|---|---|---|---|
| A | 2 | 10 mg/mL microsphere | 20 µg | 8 | 5 |
| B | 2 | 10 mg/mL microsphere | 20 µg | 31 | 5, 29 |
| C | 2 | 10 mg/mL microsphere | 20 µg | 60 | 5, 29, 54 |
| D | 2 | 10 mg/mL microsphere | 20 µg | 93 | 5, 29, 54, 86 |
| E | 2 | 10 mg/mL microsphere | 20 µg | 92* | 5, 29, 54, 86* |
| F | 2 | 100 mg/mL microsphere | 200 µg | 8 | 5 |
| G | 2 | 100 mg/mL microsphere | 200 µg | 31 | 5, 29 |
| H | 2 | 100 mg/mL microsphere | 200 µg | 60 | 5, 29, 54 |
| I | 2 | 100 mg/mL microsphere | 200 µg | 93 | 5, 29, 54, 86 |
| J | 2 | 100 mg/mL microsphere | 200 µg | 93 | 5, 29, 54, 86* |

[a]Both eyes by subconjunctival injection unless indicated otherwise.
Note:
Groups A-J received a 100 µL injection of microsphere per eye.

As shown by Table 4 each of the twenty rabbits received a single bilateral subconjunctival injection of a brimonidine tartrate containing microsphere formulation.

We determined that since the specific receptor target of brimonidine located in retina and iris-ciliary body for optic neuroprotection requires a brimonidine concentration ≥2 nM, a ten-fold higher concentration (10-20 nM; 3-6 ng/mL) from administration of a sustained release microspheres was therefore a preferred target concentration to be obtained.

The amount of brimonidine tartrate loaded into the sustained release microspheres was based on a vitreal clearance (0.487 mL/day) and the desired target therapeutic concentration for the brimonidine. Given the relationship, $C_{SS}=R_o/Cl$, where $R_o$=delivery rate, $C_{SS}$=steady-state concentration, and Cl=vitreal clearance, the required release rate of brimonidine from a drug delivery system over a 3 month period of time was calculated to be 1.46-2.92 ng/day. We determined that the 10 mg/mL and 100 mg/mL microsphere suspensions provided release rates of 1.4 and 14 µg brimonidine/day for 60 days.

Subconjunctival injection of the PLA microsphere suspensions was carried out as follows for the 10 mg/mL (20 µg brimonidine tartrate) and 100 mg/mL (200 µg brimonidine tartrate) microspheres. The bulbar conjunctiva in the dorsotemporal quadrant was elevated using forceps. The microspheres or placebo was injected into the subconjunctival space. The 10 mg/mL microsphere was administered at a dose volume of 100 µL.

Example 3

Intraocular Brimonidine Poly Lactic Acid Implants (Rabbits)

I. Sub-Tenon Placement

A. In a first experiment brimonidine tartrate PLA implants were implanted in an anterior sub-Tenon space. Either three or six brimonidine tartrate implants (each implant comprising 400 µg of the brimonidine tartrate) were implanted in the anterior sub-Tenon region superotemporally 3-4 mm from the limbus of the right eyes of New Zealand white in rabbit eyes (implant placement is shown by the photograph at the lower right hand corner of FIG. 1). Three implants (1200 ug total dose therefore) were placed in 3 rabbits, six implants (2400 ug total dose therefore) were placed in three rabbits, and placebo implants were placed in three rabbits.

FIG. 1 shows that placement of the implants resulted in a reduction in the intraocular pressure over a 50-day period, and that a dose response occurred. IOP was measured using a pneumatonometer.

The implants were placed in the anterior sub-Tenon's space by picking up the conjunctiva approximately 3-4 mm posterior to the limbus with a toothed forceps. Using a Wescott scissors, the conjunctiva was entered and the Tenon's fascia was dissected off of the episclera to form a pocket where the implants were placed. The sub-Tenon's pocket was approximately the same size as three implants placed side by side. This positioning kept the implants secured in the dissected region and the chance for migration posteriorly was reduced. Typically, the implants are not sutured on to the episclera, for non-bioerodible implants, suturing would be optional. In addition, suturing of the conjunctival wound is optional and was performed using a single 9-0 vicryl in an x-fashion. In rabbits receiving a total of 6 implants, the other 3 implants were placed sub-tenon in the superonasal quadrant using the same procedure.

Significantly, throughout the observation period the eyes of the rabbits were white and there were no signs of clinically toxicity. The area of slight redness on the surface of the eye in the photograph in FIG. 1 to the right of the three 400 µg brimonidine implants is unrelated to the presence of the implant, as this area is usually so colored or shaded as it is a vascularized site of rectus muscle tendon insert on the sclera. This photograph was taken on day 21. Significantly, the eyes of the rabbits had the same appearance as in this FIG. 1 photograph after about day 7 after the implant administration, and the eyes retained this white appearance (hi or hi normal OSH score) thereafter throughout the 50 day observation period, and there were no signs of clinical toxicity over the 50-day observation period.

The formulation of the implants was 35 wt % (400 µg) brimonidine tartrate, 40 wt % a PLA polymer (Resomer R203S) and 25 wt % as a second PLA polymer (Resomer R208). The implant weight was 1.14 mg±15%. The implant was made using a twin screw extruder. It was previously determined that single implants released in vitro the entire 400 ug of brimonidine over about a 7 month period.

Thus, in vitro studies showed that this 400 μg (35 wt %) brimonidine tartrate implant has a substantially linear release profile in which about 10% of the brimonidine was released by day 15, about 33% by day 30, about 55% by day 60, about 68% by day 90, about 75% by day 120, and about 100% of the brimonidine had been released from the implant by between about 150 to about 210 days.

Placebo implants were made the same way as were the brimonidine containing implant but comprised 62 wt % the PLA polymer Resomer R203S and 38 wt % as a second PLA polymer Resomer R208. Each individual (non-placebo) implant of the six implanted together in rabbit eyes was formulated to release (as confirmed by an in vitro release study) approximately 400 ug of the brimonidine over a period of about 7 month period, for a total release from the six implants of about 2.4 mg of the brimonidine tartrate over the seven month period. As shown by FIG. 1, these sub-tenon implants provided an anti-hypertensive effect as compared to placebo.

B. In a second experiment we administered to a sub-Tenon location of rabbit eyes brimonidine poly lactic acid wafer implants. The implants were formulated as 1 mg total weight wafers (made by a heat press process) which comprised 25 wt % brimonidine tartrate and 75 wt % the PLA polymer Resomer R206. These brimonidine implants were placed in an anterior sub-Tenon space of rabbits and were well tolerated (no hyperemia after seven days after implantation of the wafer implants) for a follow-up period of three months.

Thus, ten New Zealand white rabbits received a single bilateral sub-Tenon implantation of a poly-lactic acid wafer made by a heat press method. The rabbits were 7-10 months old and weighed 2.49-3.36 kg on the day of dosing. Each wafer had a total weight of about one mg and comprised 25 wt % (250 μg) brimonidine tartrate and 75 wt % PLA (resomer 206) (750 μg). Placebos wafers made contained 100 wt % the PLA resomer R206.

The sustained release brimonidine tartrate from the wafer implants was observed over a three month period after implant administration. This experiment was a single implant, parallel design, with five treatment groups and non-serial samples collected from each animal. Further details of the study are outlined in Table 5 below.

TABLE 5

| Group | Number of Rabbits | Treatment[a] (Day 1) | brimonidine tartrate dose | Euthanasia and Necropsy (Day After Dosing) | Ophthalmic Observation (Day After Dosing) |
|---|---|---|---|---|---|
| A | 2 | 1 mg PLA wafer | 250 μg | 8 | 5 |
| B | 2 | 1 mg PLA wafer | 250 μg | 31 | 5, 29 |
| C | 2 | 1 mg PLA wafer | 250 μg | 60 | 5, 29, 54 |
| D | 2 | 1 mg PLA wafer | 250 μg | 93 | 5, 29, 54, 86 |
| E | 2 | 1 mg PLA wafer | 250 μg | 93* | 5, 29, 54, 86* |

[a]Both eyes received by sub-Tenon implantation unless a single implantation of one wafer per eye.

As shown by Table 5 ten female rabbits were used in this study, with two rabbits in each treatment group. Each of the ten animals received a single bilateral sub-Tenon implantation of a brimonidine tartrate containing wafer formulation.

The animals received surgical implantation of an implant (wafer) into the anterior sub-Tenon space following a conjunctival incision 3 mm from the limbus and lateral to the dorsal rectus muscle. Sub-Tenon administration the brimonidine tartrate sustained release implants used in this experiment can provide sustained delivery to the retina of the brimonidine. We determined that the PLA wafers provided a release rate of 5 μg brimonidine/day over 30 days and 1.25 μg brimonidine/day out to 90 days.

Surgical sub-Tenon implantation of wafer drug delivery systems was carried out as follows. A conjunctival incision was made (3 mm from the limbus and lateral to the dorsal rectus muscle) and the bulbar conjunctiva in the dorsotemporal quadrant was elevated using forceps. A sterile forceps, holding the appropriate drug delivery system article or placebo was introduced (administered) into the anterior sub-Tenon space. The conjunctivae were closed with 10-0 prolene suture material.

These experiments determined that a drug delivery system can be implanted sub-Tenon's to provide therapeutic levels of an active agent (such as brimonidine) to the anterior chamber of the eye (for example to treat an elevated intraocular pressure) and/or to the posterior chamber of the eye to treat a retinal condition.

II. Suprachoroidal Placement

Figure 5:
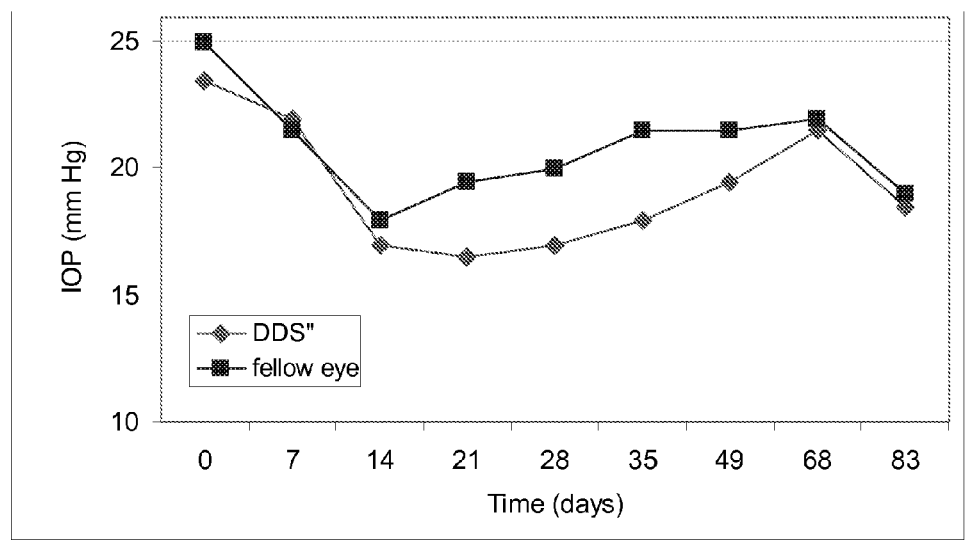
FIG. 5 is a graph which shows the IOP in mm Hg on the Y axis versus time in days on the X axis for normotensive rabbits who had two 200 μg brimonidine rod shaped implants administered to an anterior suprachoroidal location.

In this experiment a New Zealand white rabbit eye received brimonidine tartrate rod shaped implants. Each implant contained 200 μg of brimonidine tartrate as 35 wt % of the total implant weight. 40 wt % of the implant was the PLA Resomer R203S, and the remaining 25 wt % was the PLA Resomer R208. The implants were made by a melt extrusion process using a twin-screw extruder. The weight of each implants was about 0.571 mg±15%. The implants were placed in the anterior suprachoroidal space superotemporally 3-4 mm from the limbus in the right eye. Two implants (400 ug total dose) were placed into a rabbit eye into the anterior suprachoroidal space using forceps after the implant site was accessed and exposed with a 2.3 mm wide crescent angled ophthalmic blade. The incisional area was closed with one absorbable suture. The suprachoroidal space is located between the sclera and the choroid. Each implant released in vitro approximately 200 ug of drug over about a 3 to 4 month period. FIG. 5 shows that the implants provided a reduction in the intraocular pressure over about 35 days with some residual IOP lowering effect seen out to about 83 days.

III. Intrascleral Placement

A New Zealand white rabbit had two 200 μg brimonidine tartrate implants placed intrascleral superotemporally 3-4 mm from the limbus in the right eye (anterior intrascleral location). Each implant consisted of 200 μg (35 wt %) brimonidine tartrate, 40 wt % the PLA Resomer R203S, and 25 wt % the PLA Resomer R208. The implants were made by a melt extrusion process using a twin-screw extruder. The weight of one implant was about 0.571 mg±15%. The implants were placed in the scleral pocket with forceps.

Figure 4:
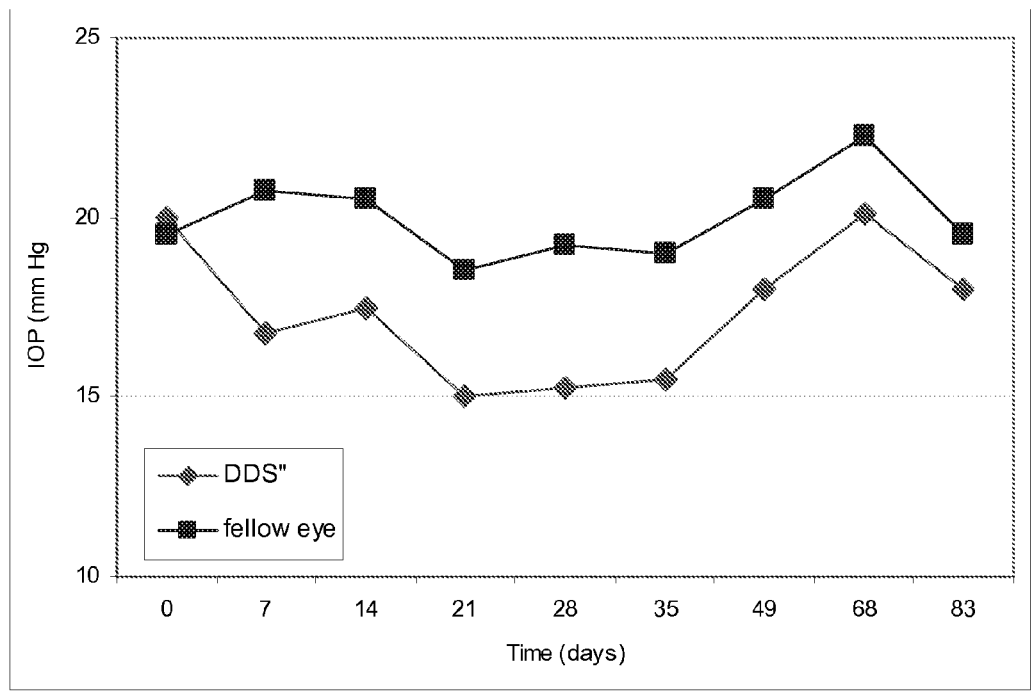
FIG. 4 is a graph which shows the IOP in mm Hg on the Y axis versus time in days on the X axis for normotensive rabbits who had either two 200 μg brimonidine rod shaped implants administered (the lower graph line) to an anterior intrascleral location or placebo ("fellow eye") implants administered.

The implants released in vitro the 200 μg of brimonidine from each implant over about a 3 to 4 month period. Two implants (400 μg total dose) were placed in one rabbit eye in an intrascleral tunnel formed with a 2.3 mm wide crescent angled ophthalmic blade to about a 50% depth into the sclera. The implants were placed in the scleral pocket so made and the incisional area was closed with one absorbable suture. FIG. 4 demonstrates a reduction in the intraocular pressure over about 35 days with a gradual return towards baseline.

Example 4

Sub-Tenon Bimatoprost PLGA Implants (Dogs)

In this experiment biodegradable rod shaped bimatoprost containing implants were administered to the eyes of six dogs. Two dogs each received three side by side placebo implants, two dogs received three side by side drug containing implants, and the remaining two dogs each received six side by side drug containing implants. Each implant consisted of 15 wt % (150 μg) bimatoprost, 75 wt % RG752S and 10 wt % PEG3350. The weight of each implant was about 1 mg. RG752S is a poly(D,L-lactide-co-glycolide) polymer in a D,L-lactide: glycolide ratio of 75:25. RG752S has an inherent viscosity of between about 0.16 to 0.24 dl/g in 0.1% chloroform at 25° C., and is available from Boehringer Ingelheim Chemicals, Inc., Petersburg, Va. PEG-3350 is a widely available synthetic polyglycol with the formula $[HO(C_2H_40)_n$, and an average molecular weight of 3350.

Figure 2:
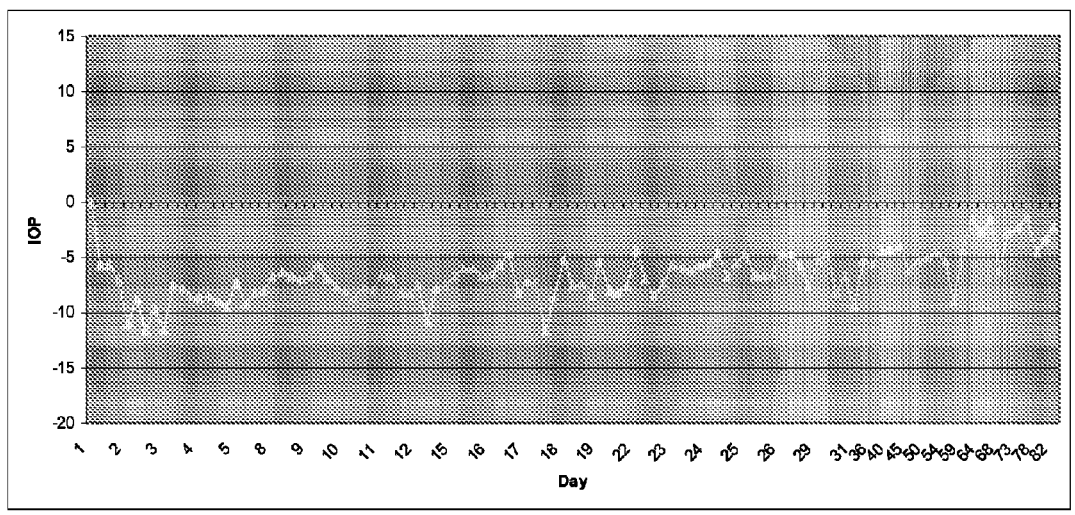

The implants were made by a melt extrusion process. It was previously determined that single implant released in vitro about the 150 μg of bimatoprost over a period of 2 to 3 months, with about 10% of the bimatoprost having been released after about ten days, about 35% after about 20 days, about 50% after about 30 days, and about 80% released after about 40 days in vitro. In this experiment bimatoprost-implants were placed in dog (beagle) eyes in the anterior sub-Tenon's region superotemporally 3 to 4 mm from the limbus in the left eye. FIG. 2 for one of the dog eyes implanted shows that a reduction in the intraocular pressure of up to about 12 mm Hg occurred and that an IOP reduction was observed over the entire 82 day period after brimonidine implant administration to this dog eye.

Example 5

Sub-Conjunctival Brimonidine Poly Ortho Ester Implants (Rabbits)

In this experiment we determined that a drug delivery system based upon a poly ortho ester polymer can be subconjunctivally implanted to provide therapeutic levels of an active agent (such as brimonidine) to the anterior chamber of the eye (for example to treat an elevated intraocular pressure) and/or to the posterior chamber of the eye to treat a retinal condition. In this Example several polyorthoester (POE) implants (rods) were made and three different POE formulation implants were inserted intraocularly into the subconjunctiva of rabbit eyes. Details of two of the three POE implant formulations (Lot 1 and Lot 2) inserted is provided below.

Each of the POE implant formulations made were 1 mg rod shaped implants made by a melt extrusion process, as set forth previously. Each implant consisted of 20 wt % (or (200 μg)) brimonidine and 80 wt % (or 800 μg) POE. The POE was a poly(orthoester) polymer made by condensation polymerization of 3,9-diethylidene-2,4,8,10-tetraoxaspiro[5.5]undecane (DETOSU), cyclohexanedimethanol (CDM), triethylene glycol (TEG) and 1,10-decanediol (DD). Triethylene glycol glycolide (TEG-GL) was added as a latent acid catalyst to initiate hydrolysis of the POE backbone. The POE polymer molecular weight was about 30,000 to about 35,000 Daltons.

In this experiment New Zealand white rabbits received a single bilateral subconjunctival implantation of the poly-ortho-ester rod implant. Placebos made contained 100 wt % the POE polymer.

The sustained release of brimonidine tartrate from the POE implants was observed over a three month period after implant administration.

In all 30 female New Zealand White rabbits were used in this experiment (ten rabbits each received one of the three brimonidine POE implant formulations). The animals were 7-10 months old and weighed 2.49-3.36 kg on the day of dosing. The study carried out was a single implant, parallel design study. Further details of the study are outlined in Table 6 below for two of the three POE implant formulations used.

TABLE 6

| Group | Number of Rabbits | Treatment[a] (Day 1) | brimonidine tartrate Dosed | Euthanasia and Necropsy (Day After Dosing) | Ophthalmic Observation (Day After Dosing) |
|---|---|---|---|---|---|
| A | 2 | 1 mg POE-Lot 1 Implant | 200 μg | 8 | 6 |
| B | 2 | 1 mg POE-Lot 1 Implant | 200 μg | 31 | 6, 31 |
| C | 2 | 1 mg POE-Lot 1 Implant | 200 μg | 60 | 6, 31, 55 |
| D | 2 | 1 mg POE-Lot 1 Implant | 200 μg | 93 | 6, 31, 55, 87 |
| E | 2 | 1 mg POE-Lot 1 Implant | 200 μg | 93* | 6, 31, 55, 87* |
| F | 2 | 1 mg POE-Lot 2 Implant | 200 μg | 8 | 6 |
| G | 2 | 1 mg POE-Lot 2 Implant | 200 μg | 31 | 6, 31 |
| H | 2 | 1 mg POE-Lot 2 Implant | 200 μg | 60 | 6, 31, 55 |
| I | 2 | 1 mg POE-Lot 2 Implant | 200 μg | 93 | 6, 31, 55, 87 |
| J | 2 | 1 mg POE-Lot 2 Implant | 200 μg | 93 | 6, 31, 55, 87* |

[a]Both eyes received by subconjunctival implantation a single implanted rod in each eye.

The POE of the Lot 1 implants consisted of (in relative weight proportions) 98 DETOSU, 40 CDM, 45 DD 10 TEG and 5 TEG GL. The POE of the Lot 2 implants consisted of (in relative weight proportions) 98 DETOSU, 40 CDM, 55 DD 0 TEG and 5 TEG GL.

Each of rabbit received a single bilateral subconjunctival implantation of a brimonidine tartrate containing rod formulation. The Lot 1 and Lot 2 two POE rod implants provided in vivo brimonidine release rates of 2.2 and 2.6 µg/day, respectively.

The rabbits received subconjunctival surgical implantation of a POE implant (rod) into the subconjunctival space following a conjunctival incision 3 mm from the limbus and lateral to the dorsal rectus muscle, and the bulbar conjunctiva in the dorsotemporal quadrant was elevated using forceps. A sterile forceps, holding the appropriate drug delivery system article or placebo, was introduced (administered) into the subconjunctival space. The conjunctivae were closed with 10-0 prolene suture material.

Example 6

Intraocular Bimatoprost Microspheres (Dogs)

Six dogs (beagles) had bimatoprost microspheres injected into the anterior sub-Tenon's region superotemporally 3-4 mm from the limbus in the left eye using a syringe with a 25 gauge needle.

The microspheres were PLGA (75:25-acid) microspheres made by Brookwood Pharmaceuticals using a cooled PLG solution process. The microspheres contained 6.8 wt % bimatoprost. The in vitro release rates showed that over 13 days, the cumulative release of bimatoprost was 25%. The total release time was extrapolated to be approximately 6-8 weeks.

Figure 3:
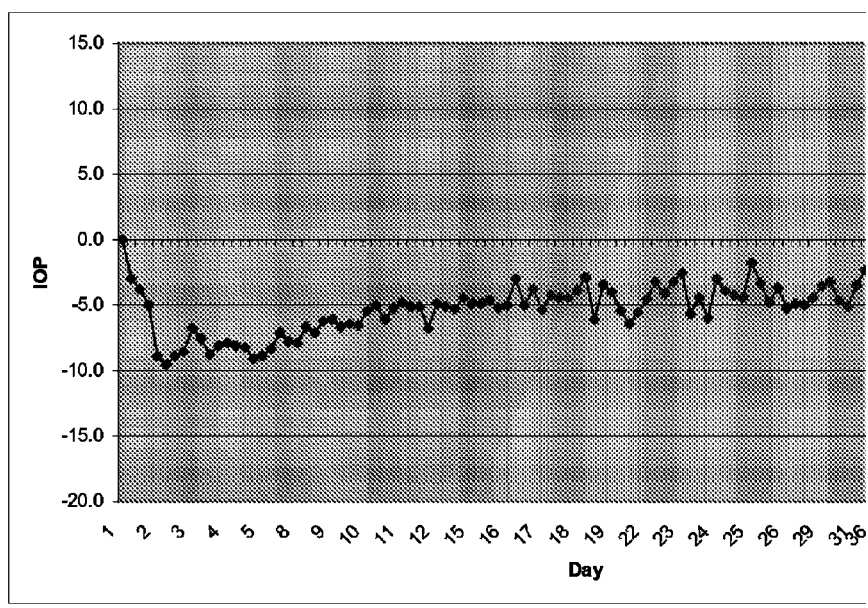

A total of 6 dogs were used in this study. Three dogs received a microsphere dose containing a total of 300 µg of bimatoprost and three dogs received a microsphere dose containing a total of 600 µg of bimatoprost. FIG. 3 displays graphically the reduction of IOP from baseline in a dog eye which received a 600 µg microsphere formulation injection and that this bimatoprost microsphere in this animal provided an IOP reduction of up to 10 mm Hg over a 36 day observation period.

Figure 6:
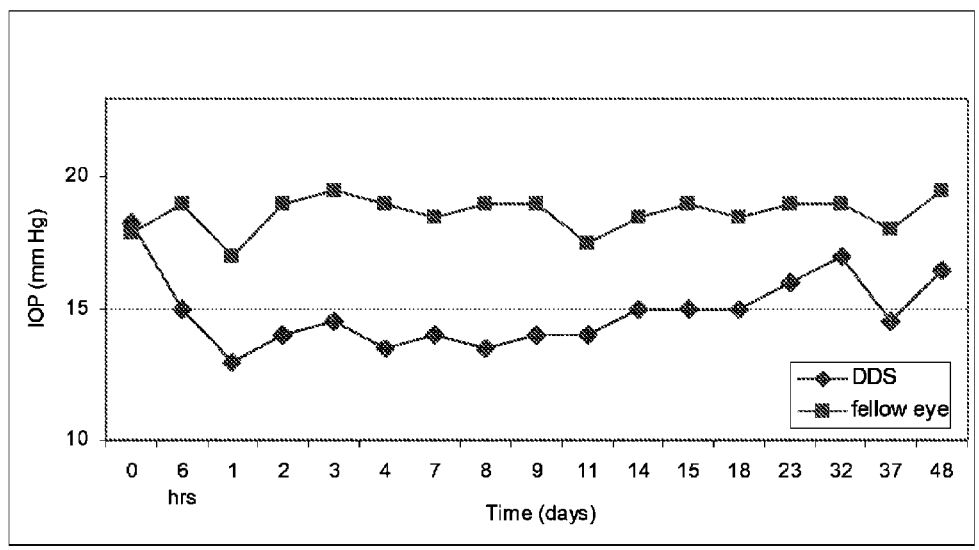
FIG. 6 is a graph which shows the IOP in mm Hg on the Y axis versus time in days on the X axis for dogs who had either 200 μg lipophilic prostamide (20 wt %) containing disc shaped (compression) implants ("DDS") placed in an anterior intrascleral location or placebo ("fellow eye") implants administered at the same location in the dog's other (fellow) eye.

In a second experiment two dog (beagles) had a lipophilic prostamide (20 wt %, about 200 µg of drug in a 1 mg implant) two disc implants (2) placed in the anterior sub-Tenon's region superotemporally 3-4 mm from the limbus in the left eye of two dogs. A single implant released in vitro approximately 100-200 ug of drug over a period of about one month. For a control, placebo implants were placed in the same location in two other dogs. FIG. 6 demonstrates a reduction in the intraocular pressure as compared to placebo ("fellow eye") over the 50 day observation period.

The implants were placed in the anterior sub-Tenon's space by picking up the conjunctiva approximately 3-4 mm posterior to the limbus with a toothed forceps. Using a Wescott scissors, the conjunctiva was entered and the Tenon's fascia was dissected off of the episclera to form a pocket where the implants are placed. The implants were placed in the pocket on the episclera and the conjunctiva was closed with an interrupted 9-0 vicryl suture.

The lipophilic prostamide used was a synthetic prostamide analog with ocular hypotensive activity. The chemical name of the lipophilic prostamide used is 7-{2-[5-(3-Fluoro-4-methyl-thiophen-2-yl)-3-methoxy-pent-1-enyl]-3,5-dihydroxy-cyclopentyl}-hept-5-enoic acid ethylamide. The molecular formula is $C_{25}H_{38}F_1N_1O_4S_1$ and the molecular weight is 467.64. The structural formula of the lipophilic prostamide used is

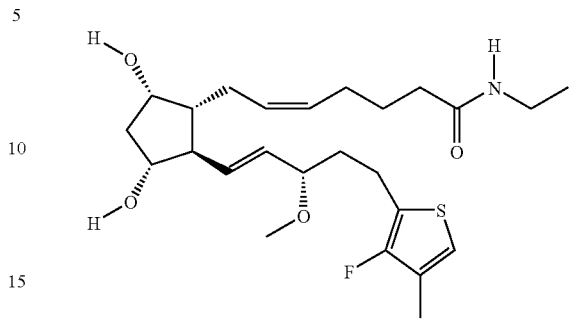

The implants were made using a direct compression process. First the lipophilic prostamide was mixed with 50:50 poly(lactide-co-glycolide) (Boehringer-Ingelheim, RG502) at 20 wt %. The mixture was then directly compressed into a pellet on a Parr Pellet Press. For each implant, 5 mg of the 20% lipophilic prostamide and RG502 blend was loaded into a 3 mm die. A punch then compressed the blend into a tablet by exerting 150 pounds of pressure over 10 seconds. The final assay value of the implant was 1.12 mg of the lipophilic prostamide per 5 mg of implant.

An in vitro release study was carried out by placing one implant into 20 mL of isotonic phosphate buffered saline (receiver media) in a 20 mL glass scintillation vial. The implant was shaken at 37° C. and the receiver media completely exchanged with new isotonic phosphate buffered saline at the appropriate time points. Each aliquot removed was assayed for the lipophilic prostamide released by HPLC. We found that after six days about 35-40% of the lipophilic prostamide was release in this in vitro assay.

Example 7

Intravitreal Brimonidine Implant

In this experiment brimonidine drug delivery systems were made for intravitreal administration to treat acute and chronic retinal injuries, diseases and conditions, improve visual acuity and contrast sensitivity in patients with diabetic macular ischemia, to provide retinal neuroprotection and prevent changes associated with diabetic retinopathy, such as microaneurysms, which can be associated with vascular leakage and macular edema.

Cylindrical (rod shaped) implants suitable for intravitreal administration were made by dispersing the therapeutic agent brimonidine tartrate in a poly(D,L-lactide) biodegradable polymer with or without a poly(D, L-lactide-co-glycolide) biodegradable polymer. The implants were made by melt extrusion using a piston driven extruder or a twin-screw extruder/microcompounder (Daca). The brimonidine implant made on the piston extruder can release the brimonidine over about a 1 month period. The implant made on the Daca extruder can release the brimonidine over a 3 to 4 month period. The implant is about 0.46 mm (0.457 mm±0.013 mm) in diameter and the length ranges from about 2 mm to about 6 mm to accommodate the different doses. The weight of the implant ranges from approximately about 0.4 mg to about 1.2 mg.

The low-concentration (50 µg brimonidine tartrate) implants were made on a piston extruder. The brimonidine and the polymers were mixed and blended in a stainless steel mixing capsule mounted on a Turbula shaker (Glenn Mills Inc., Type T2F) well prior to being added to the extruder barrel followed by heating the mixture and then forcing the heated mixture through a die by a mechanically driven cam.

The Daca extruder implants were made by mixing and blending the brimonidine and the polymers in the Turbula shaker. The powder blend was then added to the Daca twin-screw extruder/microcompounder incrementally. The extrusion barrel temperature was controlled within 87 to 93° C. Once the extruder temperature was set it is capable of maintaining the barrel temperature within ±1° C. of the set point. The resulting filaments were cut to length to produce a 2 mm to 6 mm long implant weighing from about 0.4 mg to about 1.2 mg depending on the desired dose. The Daca made implants were smoother and less porous than the implants made with the piston extruder. This results in a slower permeation of the medium into the implant and a consequently slower drug release. The implants were cylindrically-shaped solid implants with brimonidine tartrate dispersed in a biodegradable polymer matrix. No solvents or other processing aids were used in either process.

There are two embodiments of these implants. A low-concentration formulation implant that delivers 50 or 100-µg doses of the brimonidine tartrate and a high-concentration formulation implant which delivers 200 or 400 µg doses of brimonidine tartrate. The dose is determined by the length of the DDS implant for each respective formulation. Thus, the 50-µg implant is half as long as the 100-µg implant and the 200-µg implant is half as long as the 400-µg implant.

The compositions of the low-concentration and high-concentration formulations are provided in Table 7 below.

TABLE 7

Compositions of Brimonidine Implants

| Formulation | Brimonidine Tartrate µg | Brimonidine Tartrate wt % | R203S Poly(D,L-Lactide) wt % | R208 Poly(D,L-Lactide) wt % | RG502H Poly(D,L-Lactide-co-glycolide) wt % |
|---|---|---|---|---|---|
| Low Concentration | 50 or 100 | 12 | 53 | 25 | 10 |
| High Concentration | 200 or 400 | 35 | 40 | 25 | 0 |

The implants can be intravitreally administered using one or more of the applicators shown in related U.S. patents and published U.S. Pat. Nos. 6,899,717; 7,090,681; 2005 0203542, and; 2005 01543399. The applicator comprises a needle with a canula which contains the implant. The needle can be a 22-gauge, thin-wall, hypodermic needle, externally lubricated with Dow 360CF silicone oil. A silicone rubber sleeve can be placed over the needle from the hub to a cut-out in the needle. The sleeve can be designed with a small ring at the distal end that fits into the cut-out of the needle to hold the implant in place. The sleeve can remains outside the eye and contacts the conjunctiva during insertion.

Three polymer excipients were used in to make the two different formulations of our brimonidine intravitreal implants. One formulation delivers the 50 and 100 µg doses of brimonidine tartrate and the other formulation delivers the 200 and 400 µg doses of brimonidine tartrate. The lower concentration implant formulation contained two different molecular weight poly(D,L-lactide) (PLA) biodegradable polymers (Resomer R203S and Resomer R208) and a 50:50 poly(D,L-lactide-co-glycolide) (PLGA) biodegradable polymer (Resomer RG502H). The higher concentration formulation contained the same two biodegradable poly(D,L-lactide) polymers as the low concentration formulation, but does not contain the PLGA polymer. All the polymer excipients are manufactured under cGMP conditions by Boehringer Ingelheim.

The implant can be made with the PLA polymers: (1) Resomer® R203 and Resomer® R206; (2) Resomer® R203S and Resomer® R208, or (3) Resomer® R203S, Resomer® R208, and Resomer® RG502H (the later being a poly(D,L-lactide-co-glycolide) copolymer).

Our implant can be made using a piston extruder as a blend of two PLA polymers, Resomer R203 and Resomer R206, and 200 µg of brimonidine tartrate, as shown in Table 8 below.

TABLE 8

Composition of Brimonidine Implants

| Weight Percent Brimonidine Tartrate | Weight Percent Resomer ® R203 | Weight Percent Resomer ® R206 |
|---|---|---|
| 20 | 40 | 40 |
| 20 | 60 | 20 |

The low-concentration formulation is 12% brimonidine tartrate and the high-concentration formulation is 35% brimonidine tartrate. In general, implants with a drug load of less than 20% do not have sufficient drug at the surface of the implant to release drug early in the dissolution so a hydrophilic PLGA polymer is added to the low-concentration matrix to facilitate the drug release early in the dissolution. The brimonidine tartrate dose in the implant was determined by the length of the implant for each respective formulation. For example, the 50-µg implant is half as long as the 100-µg implant and the 200-µg implant is half as long as the 400-µg implant. The properties of the two formulations are shown in Table 9 below.

TABLE 9

Properties of Brimonidine Implants

| Property | Formulation | | | |
|---|---|---|---|---|
| | Low Concentration | | High Concentration | |
| BT Dose, µg | 50 | 100 | 200 | 400 |
| BT Concentration, % | 12 | 12 | 35 | 35 |
| Density, g/mL | 1.25 ± 0.05 | 1.25 ± 0.05 | 1.30 ± 0.05 | 1.30 ± 0.05 |
| Length, mm | 2.03 | 4.06 | 2.68 | 5.36 |
| Diameter, mm | 0.460 | 0.460 | 0.460 | 0.460 |
| Weight, mg | 0.417 | 0.834 | 0.572 | 1.14 |
| Sur/vol, cm$^{-1}$ | 97 | 92 | 95 | 91 |

[1]Accelerated Conditions = Shaking Water Bath at 42° C. and 50 rpm. Release Medium is PBS (0.01M) pH 7.4 containing 0.5% Triton X-100. Real-Time Conditions = Shaking Water Bath at 37° C. and 50 rpm. Release Medium is PBS (0.01M) pH 7.4.

TABLE 10

Quantitative Composition of 50 μg Brimonidine Implants

| Ingredient | Concentration, % w/w | Concentration, mg/g | Amount (g) for a 10-g Batch |
|---|---|---|---|
| Brimonidine Tartrate | 12 | 120 | 1.2 |
| Resomer ® R203S, Poly (D,L-lactide) | 53 | 530 | 5.3 |
| Resomer ® R208, Poly (D,L-lactide) | 25 | 250 | 2.5 |
| Resomer ® R502H, Poly (D,L-lactide-co-glycolide) | 10 | 100 | 1.0 |

TABLE 11

Quantitative Composition of 100-μg Brimonidine Implants

| Ingredient | Concentration, % w/w | Concentration, mg/g | Amount (g) for 10-g Batch |
|---|---|---|---|
| Brimonidine Tartrate | 12 | 120 | 1.2 |
| Resomer ® R203S, Poly (D,L-lactide) | 53 | 530 | 5.3 |
| Resomer ® R208, Poly (D,L-lactide) | 25 | 250 | 2.5 |
| Resomer ® R502H, Poly (D,L-lactide-co-glycolide) | 10 | 100 | 1.0 |

TABLE 12

Quantitative Composition of 200-μg Brimonidine Implants

| Ingredient | Concentration, % w/w | Concentration, mg/g | Amount (g) for a 10-g Batch |
|---|---|---|---|
| Brimonidine Tartrate | 35 | 350 | 3.5 |
| Resomer ® R203S, Poly (D,L-lactide) | 40 | 400 | 4.0 |
| Resomer ® R208, Poly (D,L-lactide) | 25 | 250 | 2.5 |

TABLE 13

Quantitative Composition of 400-μg Brimonidine Implants

| Ingredient | Concentration, % w/w | Concentration, mg/g | Amount (g) for a 10-g Batch |
|---|---|---|---|
| Brimonidine Tartrate | 35 | 350 | 3.5 |
| Resomer ® R203S, Poly (D,L-lactide) | 40 | 400 | 4.0 |
| Resomer ® R208, Poly (D,L-lactide) | 25 | 250 | 2.5 |

The brimonidine tartrate implant accelerated drug release profile of the low concentration 50 μg brimonidine implant was determined by high performance liquid chromatography (HPLC). Drug was released over a 21-day period in a media consisting of phosphate buffered saline (PBS, pH 7.4) and 0.5% Triton® X100 in a shaking water bath maintained at 40° C. and speed of 50 rpm. The test consisted of removing aliquots of the media at Day 1, Day-10 and Day-21. At each time point the sample was injected onto the HPLC system comprised of a Waters Symmetry C-18 column (4.6×150 mm, 3.5 μm) using a mobile phase of water/acetonitrile/methanol (84/8/8, v/v/v) containing 17 mM potassium phosphate buffer and 0.24 mM heptanesulfonic acid (sodium salt), pH adjusted to 3.0 with phosphoric acid.

It took about 22 days for the 50 μg of brimonidine tartrate to be completely released from the implant in vitro and the concentration of brimonidine detected typically ranges from approximately 0.5 ppm to 6 ppm. The therapeutic agent in our implant can alternately be a clonidine or an apraclonidine.

We found that by day 30 in vivo in the vitreous humor 95-99% of the brimonidine had been released from the piston extruded 50 μg brimonidine tartrate implant. The retina drug level from one and two implants were detectable up to Day 42 and Day 90, respectively. No systemic drug level was detected up to 200 μg dose per animal indicating selective delivery to ocular tissue was achieved.

The brimonidine implants are formulated as biodegradable solid rods that are inserted into the vitreous of the eye and slowly releases brimonidine tartrate for up to 6 months. The slow release of brimonidine tartrate from the implant can result in a sustained, nontoxic daily dose and provide long-term neuroprotection to retinal cells.

The experiments we carried out in the Examples set forth above led to our development of particular procedures for administration of an implant to anterior ocular locations, such as to an sub-Tenon location, as well as to preferred and alternate implant morphologies and contents. Firstly, we found that erosion of the conjunctiva at the edge of implant can occur and that this invariably leads to extrusion of the implant (i.e. the implant pops off the eye). To reduce the occurrence of extrusion the implant is preferably a rod or cylindrical shaped implant because such an implant shape is well accepted by the eye and easy to administer using a suitable canula diameter syringe. More preferably, all the edges of the implant (such as the two ends of a cylinder shaped implant) are rounded off, or smoothed so that the implant does not present any edges, but instead a smooth continuous curvature.

Secondly, the implant is preferably placed in an anterior sub-tenon location which is more than two mm from the limbus (i.e. more than 2 mm to up to about 10 mm from the limbus). We found that placing the implant within 2 mm of the limbus increases the chance for erosion at the edge of the conjunctiva, possibly because the upper eyelid margin can catch upon an implant at that location and these constant forces can lead to stress on the conjunctiva. Thirdly we determined that malleable implants, such as those made of silicone can reduce the occurrence of conjunctival erosions because they can conform well to the curvature of the globe the edges and therefore give a little with passing of the upper lid. Thus, a malleable implant can be suitable for administration to an anterior intraocular location which is less than 2 mm from the limbus.

Fourthly, we determined that smaller implants, such as a rod shaped implant which has a length of about 2 mm or less and a width of 0.5 mm or less is less likely to extrude. With such smaller implant a higher wt % drug load is required and/or use of multiple implants placed at the same location.

Fifthly, we found that the superior or upper part of the eye is a better location for implants administration for increasing the drug concentrations into the eye, as compared to an inferior or lower eye quadrant location. The principal elimination mechanism of the conjunctiva are through the lymphatic drainage system. The lymphatics are present in a bilayer, one fine network just below the conjunctival epithelium, another layer that communicates with the other that is located in the mid-zone of the Tenon's fascia and has lymphatic vessels that are larger in diameter. The lymphatics are located diffusely around the anterior conjunctiva and drain through larger lymphatic vessels located in both the inferotemporal region and also the inferonasal region. From here, the lymphatics merge into the cervical lymph node and medial lymph node chains, respectively. They further drain inferiorly and end up in larger lymph vessels, such as the thoracic duct, and then into to venous blood system. Since the net movement of lymph fluid on the eye is from superior to inferior (from upper to lower eye surface), placing drug delivery systems on the episclera superiorly allows for greater ocular drug contact time and this can increase drug concentrations in the eye. Conversely, placing implants inferiorly will lead to shorter contact times since the drug released is closer to the main lymphatic elimination trunks. Notably, the art teaches placing a drug delivery system implant in the inferior quadrants of the eye because the lower eyelid is less likely to cause extrusion of the implant compared with the superior quadrants for the very simple reason that the upper eyelid moves much more than the lower eyelid. Thus, our preferred superior quadrant implant placement is, for the reasons set forth above, counterintuitive.

Sixth, the addition of a sclera penetrant enhancers to the implant can be useful. Normally, the sclera is an anatomic barrier, the addition of a prostaglandin and/or a preservative, such as benzalkonium chloride, can increase drug penetration through the sclera. Our discovery is that we can have both a scleral penetration enhancer elute out of the implant as well as the active antihypertensive agent.

Seventh, we can add two or more antihypertensive agents to the implant. For example, it has been previously shown that the addition of timolol to brimonidine tartrate in a combination eye drop can enhance the IOP lowering effect. In addition, one can add a beta blocker to a prostamide/prostaglandin and this may reduce the conjunctival hyperemia. The addition of a beta blocker to either an alpha agonist or a prostamide/prostaglandin may reduce the occurrence of ocular allergy or hyperemia.

All references, articles, patents, applications and publications set forth above are incorporated herein by reference in their entireties.

Accordingly, the spirit and scope of the following claims should not be limited to the descriptions of the preferred embodiments set forth above.

We claim:

1. A method for treating glaucoma, the method comprising the step of placing multiple biodegradable rod shaped implants side-by-side into the anterior sub-Tenon's region superotemporally 3 to 4 mm from the limbus in the eye, wherein each implant consists of
   a) 15% by weight bimatoprost;
   b) 75% by weight RG752S, which is a poly(D,L-lactide-co-glycolide) polymer having a D,L-lactide:glycolide ratio of 75:25 and having an inherent viscosity of between about 0.16 to 0.24 dl/g in 0.1% chloroform at 25° C.; and
   c) 10% by weight PEG 3350.

2. A biodegradable rod shaped implant for anterior sub-Tenon administration, with a length of about 2 mm or less and a width of 0.5 mm or less, consisting of:
   a) 15% by weight bimatoprost;
   b) 75% by weight RG752S, which is a poly(D,L-lactide-co-glycolide) polymer having a D,L-lactide:glycolide ratio of 75:25 and having an inherent viscosity of between about 0.16 to 0.24 dl/g in 0.1% chloroform at 25° C.; and
   c) 10% by weight PEG 3350.

* * * * *